United States Patent
Abdolahad et al.

(10) Patent No.: US 10,591,462 B2
(45) Date of Patent: Mar. 17, 2020

(54) ELECTROCHEMICAL METHOD AND DEVICE FOR DETECTING THE EFFECT OF ANTICANCER DRUGS

(71) Applicants: Mohammad Abdolahad, Tehran (IR); Hani Shashaani, Tehran (IR); Mahsa Faramarzpour, Sari (IR)

(72) Inventors: Mohammad Abdolahad, Tehran (IR); Hani Shashaani, Tehran (IR); Mahsa Faramarzpour, Sari (IR)

( * ) Notice: Subject to any disclaimer, the term of this patent is extended or adjusted under 35 U.S.C. 154(b) by 19 days.

(21) Appl. No.: 15/447,415

(22) Filed: Mar. 2, 2017

(65) Prior Publication Data
US 2017/0176414 A1 Jun. 22, 2017

Related U.S. Application Data

(60) Provisional application No. 62/302,838, filed on Mar. 3, 2016.

(51) Int. Cl.
*G01N 33/50* (2006.01)
*G01N 27/327* (2006.01)

(52) U.S. Cl.
CPC ..... *G01N 33/5011* (2013.01); *G01N 27/3278* (2013.01)

(58) Field of Classification Search
None
See application file for complete search history.

(56) References Cited

U.S. PATENT DOCUMENTS 5,496,697 A   3/1996 Parce et al.
9,128,096 B2  9/2015 Buggy et al.

FOREIGN PATENT DOCUMENTS

CN  103954663 A  *  7/2014
WO  1998007034 A1    2/1998
WO  2000073784 A3    7/2001

OTHER PUBLICATIONS

Abiri et al., Biosens. Bioelectron. 68:577-585 (2015).*
Alexander et al (Analyst, 137: 5823-5828 (2012).*
Wang et al., Biosensors, 2(2):127-170 (2012).*
Pradhan et al., RSC Adv., 4:9432-9438 plus supplemental (2014).*
Rashid et al. J. Nanomater 2013:1-18 (2013).*
Cui et al., Anal. Chem., 78: 6347-6355 (2006).*
Autolab, Autolab Application Note EC08 (2011).*
Andreescu, Methods, 37:84-83 (2005).*
Anh-Nguyen et al., Proc. Eng., 120:928-931 (2015).*
Chen et al., Chem. Eur. J., 11:1467-1472 (2005).*
Chen et al., Sensors & Transducers, 189(6):137-142 (2015).*
El-Said et al, Biosens. Bioelectron., 26:1486-1492 (2010).*
Liu et al., Biosens. Bioelectron., 24:1305-1310 (2009).*
Namdari et al., Nanoscale Res. Lett., 11(406):1-16 (2016).*
Shen et al., Electroanal., 20(23):2526-2530 (2008).*
Chen Yi, Continuous in Situ Electrochemical Monitoring of Doxorubicin Efflux from Sensitive and Drug-Resistant Cancer Cells, Biophysical Journal, Nov. 1998, vol. 75, pp. 2255-2261.
Suijian Qi, Cell adhesion and spreading behavior on vertically aligned silicon nanowire arrays, ACS applied materials & interfaces, Nov. 24, 2008, vol. 1, Issue 1, pp. 30-34.
Pranjal Chandra, Advance Diagnosis of Drug Resistance in Cancer: Towards Point-of-Care Electronic Nanodevice, Analytical and Bioanalytical Techniques, May 7, 2015, vol. 6, Issue 3, e. 120.
Daman J. Adlam, Electrochemical monitoring of rat mammary adenocarcinoma cells: an in vitro assay for anticancer drug selection, Assay and drug development technologies, 2008, vol. 6, No. 6, pp. 795-802.
Pranjal Chandra, Ultrasensitive detection of drug resistant cancer cells in biological matrixes using an amperometric nanobiosensor, Biosensors and Bioelectronics, Mar. 2015, vol. 70, pp. 418-425.
Chunmei Yu, A new disposable electrode for electrochemical study of leukemia K562 cells and anticancer drug sensitivity test, Biosensors and Bioelectronics, Oct. 2013, vol. 53, pp. 142-147.
Haijun Zhang, Rapid diagnosis of multidrug resistance in cancer by electrochemical sensor based on carbon nanotubes-drug supramolecular nanocomposites, Jan. 2011, vol. 26, pp. 3361-3366.
Jing Zhao, An electrochemical method to assay the reversal effect on multi-drug resistance in tumor cells, Electrochemistry Communications, Jul. 2012, vol. 23, 56-58.
Hani Shashaani, Silicon nanowire based biosensing platform for electrochemical sensing of Mebendazole drug activity on breast cancer cells, Biosensors and Bioelectronics, May 2016, vol. 85, pp. 363-370.

* cited by examiner

*Primary Examiner* — Thomas J. Visone
(74) *Attorney, Agent, or Firm* — Bajwa IP Law Firm; Haris Zaheer Bajwa

(57) ABSTRACT

An electrochemical method for detecting effect of an anticancer drug on cancer cells, including: culturing a plurality of cancer cells to form cultured cells, attaching the cultured cells onto an array of silicon nanowires (SiNWs) electrodes, measuring a first electrochemical response of the attached cells onto the array of electrodes, adding an anticancer drug to the attached cells onto the array of electrodes to form drug-treated cells, measuring a second electrochemical response of the drug-treated cells, and determining the effect of the anticancer drug on the cancer cells based on a comparison of the first and the second electrochemical responses.

14 Claims, 26 Drawing Sheets

ELECTROCHEMICAL METHOD AND DEVICE FOR DETECTING THE EFFECT OF ANTICANCER DRUGS

CROSS REFERENCE TO RELATED APPLICATION

The present application claims priority from U.S. Provisional Patent Application Ser. No. 62/302,838, filed Mar. 3, 2016, entitled "Silicon nanowire based electrochemical biosensor with integrated electrodes to detect the drug resistance of cancer cells by label free approach", which is incorporated by reference herein in its entirety.

TECHNICAL FIELD

The present application generally relates to an electrochemical method for detecting the effect of an anticancer drug on cancer cells using a biosensor including integrated silicon nanowires (hereinafter "SiNWs") electrodes.

BACKGROUND

Electrochemical biosensors transduce biological interactions into detectable electrochemical signals. Biological recognitive markers (e.g. enzymes, aptamers, or antibodies) could be immobilized/integrated at the electrochemical interface to mediate the sensing procedure. However, complexity of chemical modifications and non-specific binding, reduced the reliability and commerciality of such biosensors. If label-free interactions could be applied between analytes and interface, usage of such sensors in wide variety of bio applications would be developed. Such binding must induce changing in electrochemical signal of redox reporter. Moreover, if the oxidative/reductive electrochemical responses of the analyte were unique for different biological transformations (such as metastatic progression states of a cancer cell), sensing patterns would be achieved without any requirements to complex fictionalizations.

Therefore, there is a need for a label-free electrochemical approach with a high precision and fast detecting capability to monitor and detect the electrochemical state variations of cancer cells under cancer treatments such as anticancer drugs treatments.

SUMMARY

In one general aspect of the present disclosure, an electrochemical method for detecting the effect of an anticancer drug on cancer cells is disclosed. The method may include the steps of: culturing a plurality of cancer cells onto a substrate in a set of controlled conditions to form cultured cells, attaching the cultured cells onto an array of electrodes, measuring a first electrochemical response of the attached cells onto the array of electrodes, adding an anticancer drug to the attached cells onto the array of electrodes to form drug-treated cells, measuring a second electrochemical response of the drug-treated cells, and determining the effect of the anticancer drug on the cancer cells based on a comparison of the first and the second electrochemical responses. The cancer treating effect of the anticancer drug on the cancer cells may be determined based on a comparison between the shape and value of the first and the second electrochemical responses.

In one implementation, the array of electrodes may include an array of silicon nanowires (SiNWs).

In some implementations, the cancer cells may be epithelial cancer cells and the anticancer drug may include the drugs that induce an ionic non-equilibrium state into the cancer cells.

In some implementations, the cancer cells may be cultured in a set of controlled conditions that may be included maintaining the cancer cells in a cell culture medium cells in a $CO_2$ incubator and at a temperature of about 37° C.

In some implementations, the cultured cells may be attached onto an array of electrodes via a process including detaching the cultured cells from the substrate, for example by using a trypsinizing solution, dropping the detached cells on the array of electrodes and maintaining the array of electrodes in an incubator to achieve attachment between the dropped cultured cells and the electrodes.

In some implementations, forming the anticancer drug-treated cells may take place in two steps of adding a specific amount of the anticancer drug, and maintaining the array of electrodes including the attached cultured cells with the added anticancer drug at specific conditions. In some specific examples, the amount of added anticancer drug may be in a range of about 0.1 nano-mole per liter to about 20 nano-mole per lite. In some implementations, maintaining the array of electrodes including the attached cells with the added anticancer drug may take place in an incubator at a temperature of about 37° C. for a specific time interval that may be at least about 2 hours.

In some implementations, the first and the second electrochemical responses may be a cyclic voltammetry (CV) response and/or a differential pulse voltammetry (DPV) response that can be measured using an integrated biosensor in conjunction with an electrochemical assay system, for example a cyclic voltammetric system or a potentiostat system. The integrated electrical biosensor may include a working electrode, a counter electrode and a reference electrode, those may be made of silicon nanowires (SiNWs) designed and grown on a single silicon chip.

In another general aspect of the present disclosure, a biosensor for measuring an electrical response from biological cells is described. The biosensor may include various units directed to electrical measuring the electrochemical response and example units may include a working electrode, a counter electrode and a reference electrode that may be designed and fabricated in an integrated configuration on a chip.

The above general aspect may include one or more of the following features. The working electrode may include a first array of SiNWs that being an attachment site for the biological cells. The counter electrode may include a second array of SiNWs acquiring the electrical response from the working electrode. The reference electrode may include a third array of SiNWs adjusting a specific voltage around the working and the counter electrodes.

In some implementations, the biosensor can be used in conjunction with an electrochemical assay system to measure an electrochemical response from the biological cells.

In some implementations, the first, the second and the third arrays of SiNWs may be designed and fabricated on a chip via a method including cleaning the chip to form a clean chip, passivating the surface of the clean chip to form a passivation layer on the clean chip, depositing a catalyst layer onto the passivation layer and forming SiNWs arrays on the catalyst layer.

In some implementations, a layer of silicon dioxide ($SiO_2$) may be grown onto the surface of the clean chip to form the passivation layer with a thickness in a range of about 100 nm to about 500 nm.

In some implementations, the catalyst layer with a thickness of less than about 10 nm may be deposited on the passivation layer using a sputtering system.

In some implementations, SiNWs arrays may be formed on the catalyst layer via a two-step process including graining the catalyst layer to form a patterned three catalyst islands and growing three arrays of SiNWs onto the patterned three catalyst islands.

DETAILED DESCRIPTION

Figure 1:
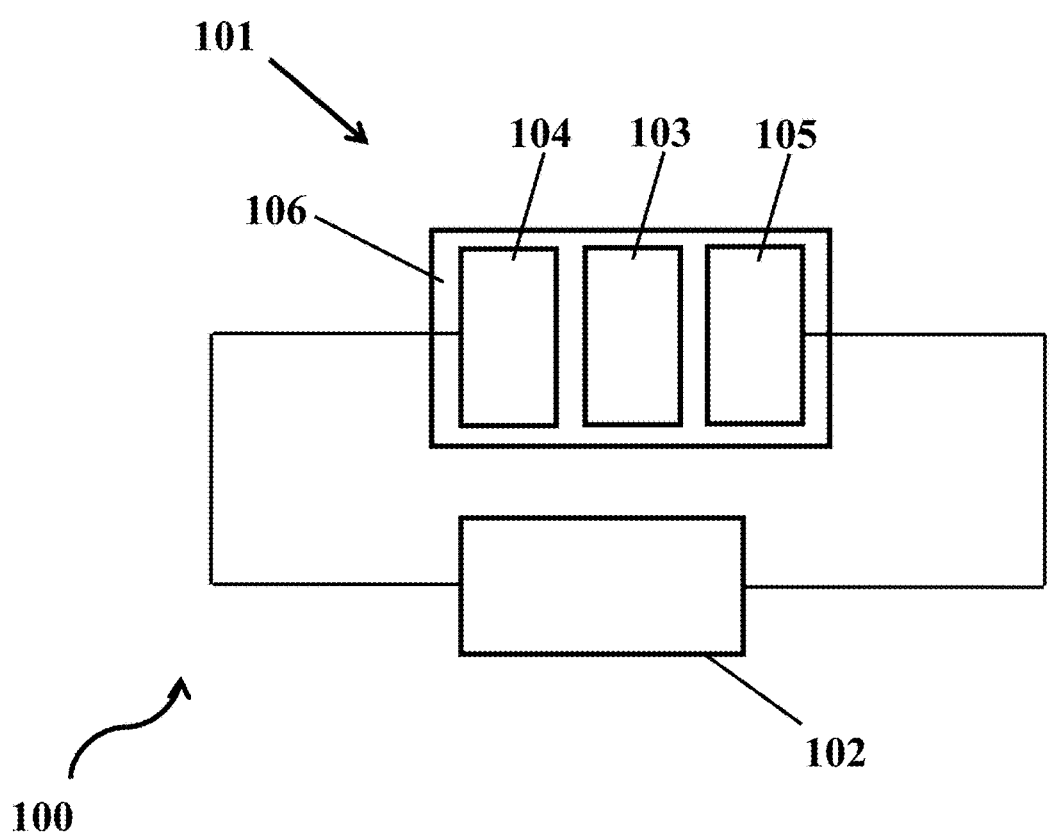
FIG. 1 illustrates a schematic of one example of an integrated biosensor used in conjunction with an electrochemical assay system, consistent with one or more exemplary embodiments of the present disclosure.

The following detailed description is presented to enable a person skilled in the art to make and use the methods and devices disclosed in exemplary embodiment of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure.

The present disclosure is not intended to be limited to the implementations shown, but is to be accorded the widest possible scope consistent with the principles and features disclosed herein.

Disclosed herein is an exemplary electrochemical method to detect the effect of an anticancer drug on cancer cells. The method can detect the anticancer drugs effect via measuring the cells ionic state changes that may be achieved via monitoring the anodic/cathodic current peaks of a plurality cell attached onto an array SiNW electrodes. The method may be considered as a new label-free electrochemical method to detect the electrochemical response of cancerous cells to a cancer treating drug.

As used herein, the "effect of an anticancer drug on cancer cells" refers to the cancer treating effect of the anticancer drug that induces a change in electrochemical properties of a biological cell that undergoes an anticancer drug treatment. Such effect is detectable through monitoring the shape and value of electrochemical responses of the treated cells, since the anticancer drug induces a change in the cells ionic state and resulting in an ionic non-equilibrium state to the cancer cells.

As used herein, the term "anticancer drug" refers to any compound or agent that can be used as therapeutic agent in cancer treatments that can perturb the ionic state of the cells.

In another aspect, the present disclosure describes an exemplary integrated electrical biosensor based on SiNWs (hereinafter "SiNW-based biosensor"). The biosensor may be used in conjunction with an electrochemical assay system instead of the system several separate electrodes.

In recent years, some generations of label free electrochemical biosensors have been developed and shed new lights in bio-analysis owing to their low cost, multiplexed detection capabilities, as well as ease of miniaturization without any additional biochemical processes. Engineering the bio-electrochemical sensing interface is crucial in such devices due to the impact of an accurate and stable response. Among various surface treatments used in interfacial modification, applying nanomaterials has presented various unique performances regarding their sizes and shapes. Great electrical conductivity, enlarged interactive surface area and well physiochemical interactions are some of the characteristics reported for many nanostructures ranged between metallic NPs to carbon nanotubes. Moreover, if the biocompatibility of nanostructures would be acceptable, sensing interfaces produced by nanostructures, would present new generation of label free biosensors for monitoring vital cells. SiNWs as a category of biocompatible nanomaterials having greatly controllable conductivity with good electron transport properties, enlarged electrochemically active area, good compatibility with silicon fabrication processes and well attachment of the cells to the outer wall of such nanostructures may be used herein to develop an effective electrochemical label free approach to monitor and detect the electrochemical assays of cancer cells during cancer treatments in a precise reliable way.

In an exemplary method, electrical responses from biological cells are measures using an exemplary biosensor. The integrated biosensor (hereinafter "SiNW-based biosensor") may include a working electrode, a counter electrode and a reference electrode, which may include arrays of SiNWs and are designed and fabricated in an integrated configuration on a single chip. The working electrode may be configured to contact to the biological cells and be an attachment site for the biological cells. The counter electrode may be configured to acquire the electrical response from the working electrode including the attached biological cells. The reference electrode may be configured to adjust a specific voltage around the working and the counter electrodes.

In some implementations, the electrical response may be an electrical current in a range of about 1 nA to about 100 μA and the specific voltage may be in a range of about −600 mV to about 600 mV.

In some implementations, the biosensor may be used in conjunction with an electrochemical assay device to measure an electrochemical response from the biological cells. For instance, the biosensor may be coupled with a cyclic voltammetric system or a potentiostat electrochemical assay system, in which the biosensor may be substituted instead of those systems electrodes to measure a cyclic voltammetry (CV) or a differential pulse voltammetry (DPV) electrochemical response.

FIG. 1 shows a schematic of an exemplary biosensor 101 used in conjunction with an electrochemical assay system 102, consistent with one or more exemplary embodiments of the present disclosure. The biosensor 101 may include three electrodes including a working electrode 103 including a first array of SiNWs, a counter electrode 104 including a second array of SiNWs and a reference electrode 105 including a third array of SiNWs that are integrated onto a chip 106. The chip 106 may be a silicon chip or a silicon wafer. The biosensor 101 may be substituted in an integrated configuration instead of three individually separated electrodes of an electrochemical assay system 102.

Figure 2A:
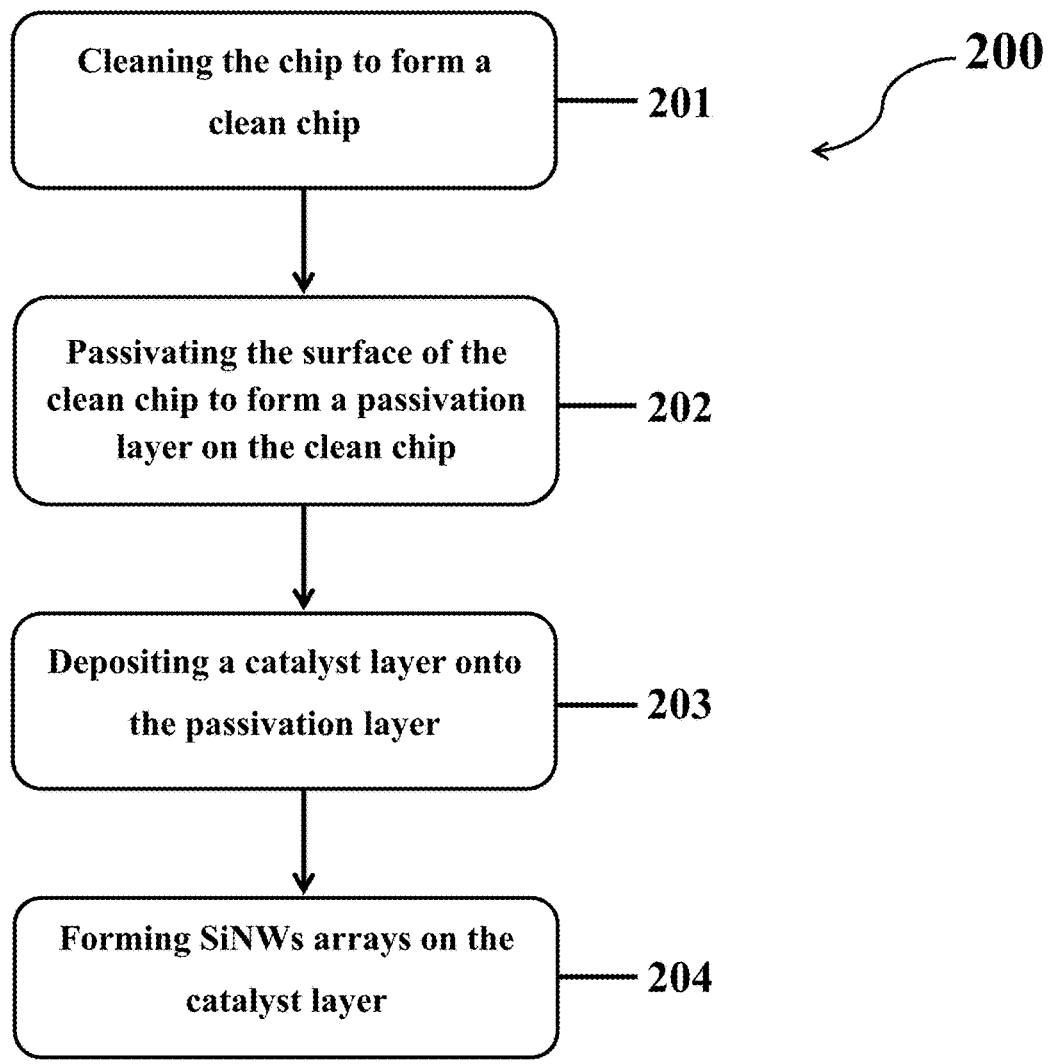
FIG. 2A illustrates an example of a method for design and fabricate three integrated SiNW arrays electrodes onto a chip, consistent with one or more exemplary embodiments of the present disclosure.

FIG. 2A shows an example of a method 200 to design and fabricate three arrays of SiNWs incorporated onto a silicon chip 106 forming three integrated electrodes of biosensor 101 on the chip, consistent with one or more exemplary embodiments of the present disclosure.

Referring to FIG. 2A, the first, the second and the third arrays of SiNWs may be designed and fabricated on a chip to form the biosensor 101 by a method including the steps of cleaning the chip to form a clean chip (step 201), passivating the surface of the clean chip to form a passivation layer on the clean chip (step 202), depositing a catalyst layer onto the passivation layer (step 203) and fourth, forming SiNWs arrays on the deposited catalyst layer (step 204).

Figure 2B:
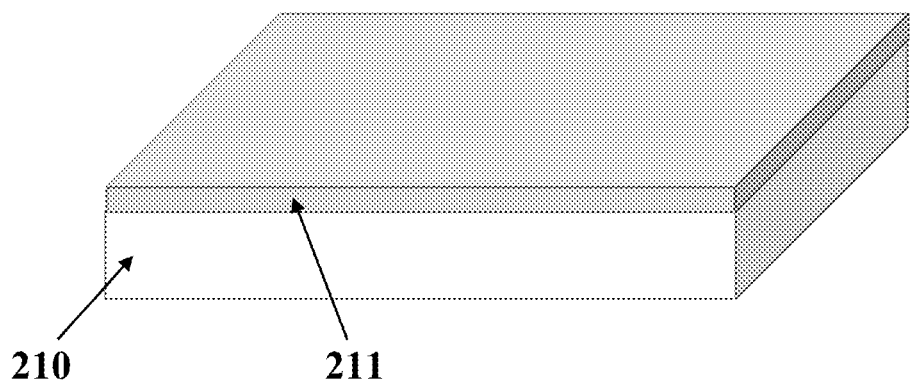
FIGS. 2B-2E illustrate exemplary steps of method for designing and fabricating three integrated SiNW arrays electrodes onto a chip, consistent with one or more exemplary embodiments of the present disclosure.

Exemplary illustration of the steps 201 to 204 are shown in FIGS. 2B-2E. In step 201, a silicon chip or a silicon wafer may be cleaned to remove impurities and form a clean chip. Subsequently, the clean chip obtained from step 201 may be passivated through step 202. In this step, a thin layer 211 of silicon dioxide ($SiO_2$) may be grown onto the surface of the clean chip 210 forming a passivation layer 211 on the clean chip as shown in FIG. 2B. The silicon dioxide ($SiO_2$) layer 211 may be grown on the clean chip 210 using a wet oxidation furnace. The passivation layer 211 may have a thickness in a range of about 100 nm to about 500 nm.

Figure 2C:
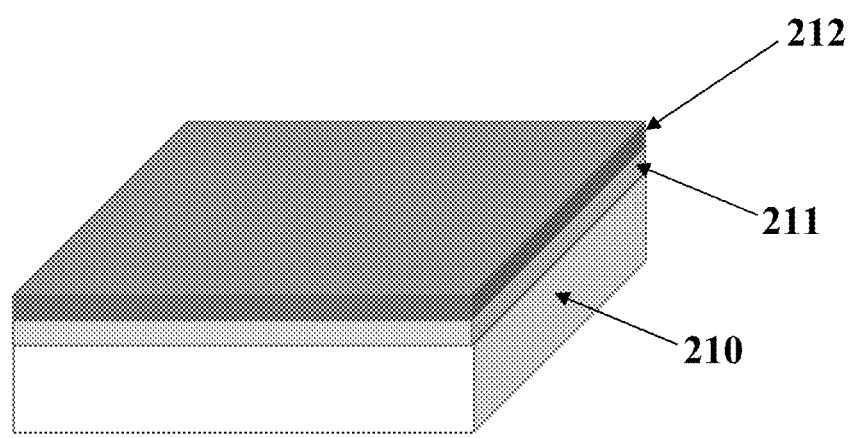

Moving on to step 203, a catalyst layer 212 may be deposited onto the passivation layer 211 as shown in FIG. 2C. The catalyst layer 212 may include a Gold (Au) layer with a thickness of about 5 nm. The catalyst layer 212 may be deposited onto the passivation layer 211 using a sputtering system and at a pressure of about 20 m Torr.

Moving on to step 204, the first, second and third SiNWs arrays may be formed on the deposited catalyst layer 212. The SiNWs arrays may be formed through a two-step process including: first, graining the catalyst layer to form three catalyst islands on the chip and second, growing three arrays of SiNWs onto the three catalyst islands.

Figure 2D:
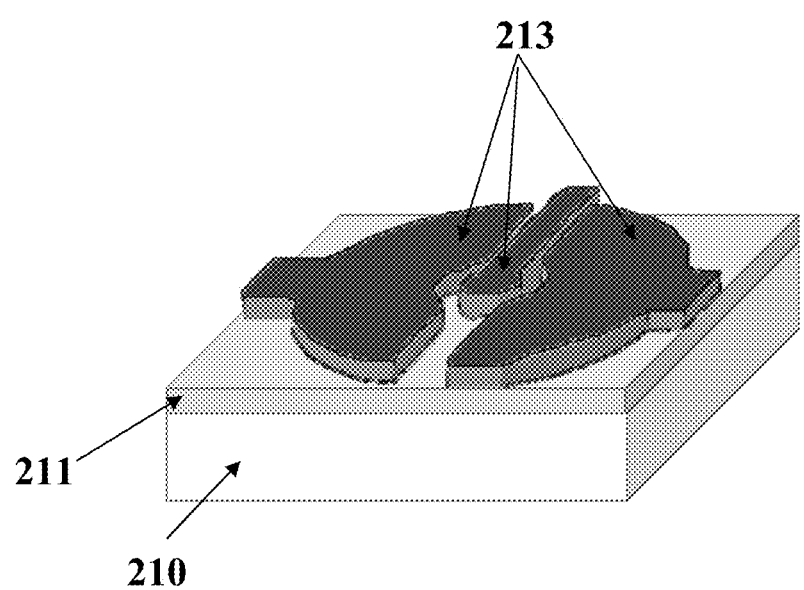
Figure 2E:
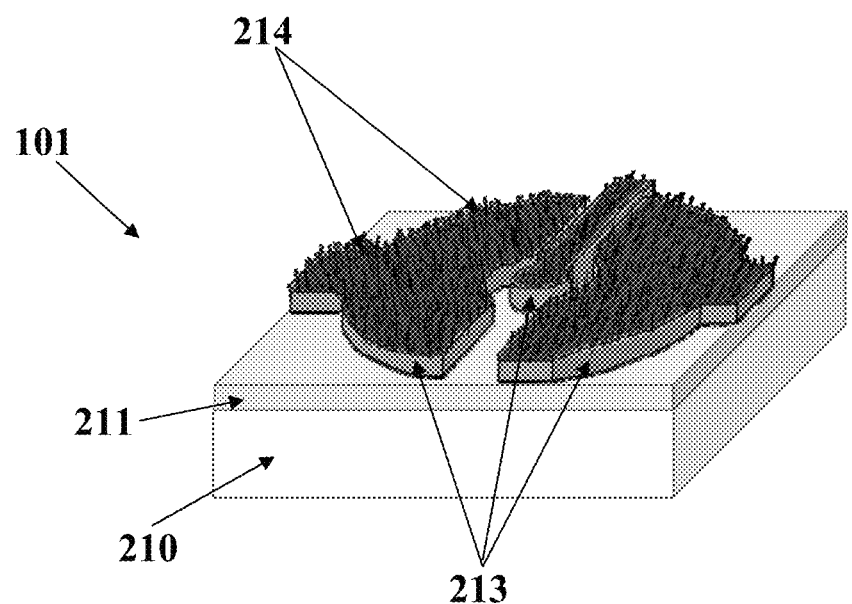

In some implementations, the SiNWs arrays may be formed on the catalyst layer using a low pressure chemical vapor deposition (LPCVD) system with a quartz tube chamber. Initially, the catalyst layer 212 may be grained to pattern the catalyst layer by architecture of the integrated work, counter and reference electrodes of biosensor 101 as shown in FIG. 2D. Correspondingly, three catalyst islands 213 may be formed on the chip. Graining the catalyst layer may be done via a thermal annealing process and in the presence of a carrier gas, for example Argon (Ar) gas. The graining of the catalyst layer may be done at a temperature range of about 450° C. to about 550° C. for a time interval about 30 minutes. Then, three arrays of SiNWs 214 may be grown onto the three catalyst islands as shown in FIG. 2E. The arrays of SiNWs may be grown onto the three catalyst islands 213 via a vapor-solid-liquid (VLS) process at a temperature of about 450° C. The VLS process may be done by assistance of a mixture of a silicon (Si) source (for example, silane ($SiH_4$)) and a carrier gas (for example, Argon (Ar). During the growth of SiNWs, Silicon nanowires may be formed on top of the three catalyst islands in their patterned regions.

It should be understood that the biosensor 101 designed and fabricated according to one or more embodiments of the present disclosure may be used to electrochemically monitor the effect of any external biochemical stimulation on the vitality and function of biological cells by tracking any ionic non-equilibrium induced in the biosensor. For instance, the anticancer drugs are one of the clinically applicable biochemical stimulators of the cancer cells.

Exemplary biosensors as manufactured with respect to methods described in connection with FIGS. 1 and 2A-2E may be utilized to detect the effect of an anticancer drug on cancer cells.

Figure 3:
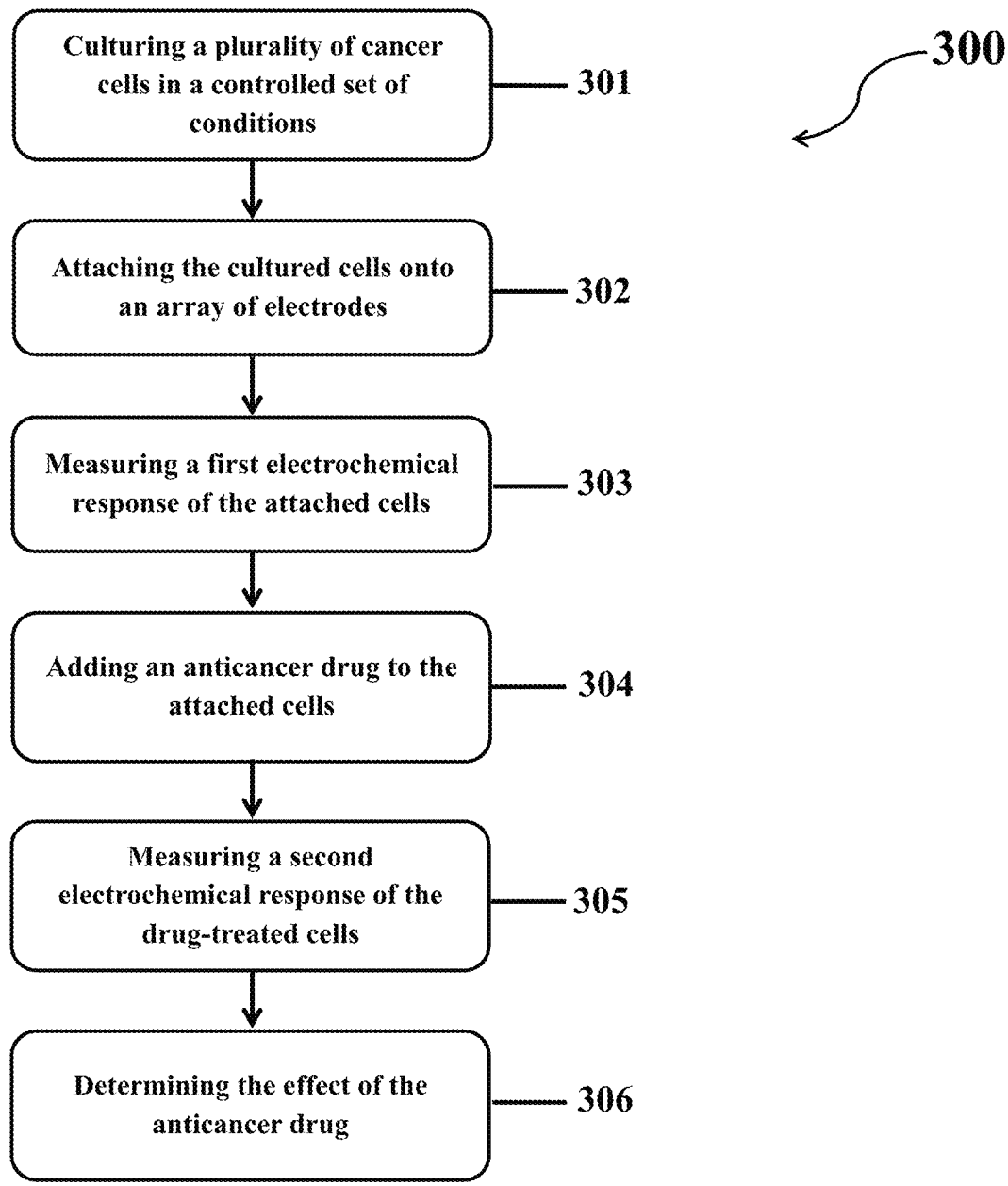
FIG. 3 illustrates an example of a method for detecting the electrochemical effect of an anticancer drug on cancer cells, consistent with one or more exemplary embodiments of the present disclosure.

For Example, FIG. 3 shows an exemplary method 300 for detecting the effect of an anticancer drug on cancer cells, consistent with one or more exemplary embodiments of the present disclosure. Method 300 may include the steps of culturing a plurality of cancer cells in a set of controlled conditions to form a plurality of cultured cells (step 301), attaching the cultured cells onto an array of electrodes (step 302), measuring a first electrochemical response of the attached cells onto the array of electrodes (step 303), adding an anticancer drug to the attached cells onto the array of electrodes to form drug-treated cells (step 304), measuring a second electrochemical response of the drug-treated cells (step 305), and determining the effect of the anticancer drug on the cancer cells based on a comparison of the first and the second electrochemical responses (step 306).

In step 301, a plurality of cancer cells may be cultured forming a plurality of cultured cells onto a for example, a glass substrate. The cells may be cultured in a set of controlled conditions including maintaining cancer cells in a $CO_2$ (about 5% $CO_2$, 95% clean air) incubator at a temperature of about 37° C. and in a culture medium, for example, a Roswell Park Memorial Institute-1640 (RPMI-1640) medium. The culture medium may be supplemented with a serum-supplement, for example, Fetal bovine serum (FBS) including Fetal bovine with an amount of about 5% and the culture medium may be further supplemented with an antibiotic in a specific amount, for example, penicillin/streptomycin antibiotic with an amount of about 1%. The fresh medium may be replaced every other day. Then, the cultured cells may be washed with a buffer solution, for example, a Phosphate-buffered saline (PBS) solution to remove the remained culture medium and supplements from the cultured cells.

In some exemplary implementations, the cancer cells may be epithelial cancer cells, for example breast cancer cells and the anticancer drug may be a drug that can induce an ionic non-equilibrium state into the cancer cells. The anticancer drug may be for example, an antitubulin drug that may perturb cells growth cycle or destroy the cells cytoskeleton, causing a change in ionic state of the cancer cells, that effects on the electrochemical characteristics and responses of the cells.

Referring to step 302, the cultured cells may be attached onto an array of electrodes. Attaching the cultured cells onto an array of electrodes may include detaching the cultured cells from the cell culture medium, dropping the detached cells on the array of electrodes, and maintaining the array of electrodes at specific conditions to obtain an attachment between the dropped cultured cells and the electrodes. The array of electrodes may include, for example, an array of silicon nanowires (SiNWs) designed and fabricated to use in electrochemical measurements, as described with respect to exemplary embodiments of the present disclosure with respect to FIGS. 1 and 2A-2E.

Accordingly, the cultured and washed cells obtained from step 301 may be trypsinized by assistance of adding a solution including trypsin and EDTA to the cultured cells in order to detach the cultured cells from the substrate. To minimize the effect of trypsinization, the procedure may be done in less than about 4 minutes at a room temperature in a range of about 20° C. to 22° C. The obtained solution having the cultured cells may be centrifuged to discard the trypsinizing solution from the detached cells. Subsequently, the detached cells may be dropped onto an array of electrodes, including for example, an array of SiNW electrodes. Then, the array of electrodes including the dropped cells may be maintained at specific conditions, for example, in an incubator at a temperature of about 37° C. and for about 4 hours to achieve an attachment between the dropped cultured cells and the electrodes.

Moving on to step 303, a first electrochemical response of the attached cells onto the array of electrodes may be measured as a control or a base value for further comparisons with a second electrochemical response of a same type that may be measured after adding an anticancer drug to the attached cells as will be described further in greater details with reference to step 305.

In step 304, an anticancer drug may be used to form anticancer drug-treated cells. Forming the exemplary anticancer drug-treated cells may include adding anticancer drug in a specific amount to the cultured cells attached onto the array of electrodes and maintaining the array of electrodes including the attached cultured cells with the added anticancer drug at specific conditions to form drug-treated cells onto the electrodes. The anticancer drug may be added in a concentration of about 0.1 nano-mole per liter to about 20 nano-mole per liter. To achieve a drug treatment affected by the added anticancer onto the attached cells onto the electrodes, the array of electrodes including the attached cultured cells with the added anticancer drug may be maintained in an incubator for at least 2 hours that may be taken long to about 12 hours or more.

Moving on to step 305, a second electrochemical response of the anticancer drug-treated cells formed during step 304 may be measured to compare with the control value measured in step 303. Moving, on stop step 306, the effect of the anticancer drug on the cancer cells may be determined based on a comparison of the first and the second electrochemical responses. Specifically, it may be determined that the anticancer drug is effective if there are changes and differences between the first and the second electrochemical responses. If it is determined that there are no changes between the first and the second electrochemical responses, it may be determined that the anticancer drug is not effective. In some exemplary cases, the anticancer drug affects the ionic equilibrium of the cells, so the treated cancer cells start to remedy the non-equilibrium status. For example, when the drug-treated cancer cells undergo a reduction reaction of cytochrome C within the cell due to an electrochemical effect of the drug, there is an accumulation of positive charge within the cells. So a change in electrical current, which may be an electrochemical response, may be formed in the solution including the drug-treated cells on the electrodes in comparison with the initial electrical current within the solution. The initial electrical current may be considered as the first electrochemical response and the second electrochemical response may include the second electrical current after drug treatment. The amount of change in electrical current due to the drug treatment may depend on the drug concentration, time of treatment, cells concentration, etc. In some examples, the first electrochemical response may include smoother curves of electrical current versus applied voltages with smaller amounts of electrical currents. After treating the cells with the anticancer drug, if the anticancer drug affect the cells, the second electrochemical response may include curves of electrical current versus applied voltages having sharp peaks in comparison with the first electrochemical response and may show larger amounts or values of electrical current, for example about 1000 times greater than those for the first electrochemical response.

Referring again to steps 303 and 304, the first and the second electrochemical responses may be for example, a cyclic voltammetry (CV) assay or a differential pulse voltammetry (DPV) response. The first and the second electrochemical responses may be measured by assistance of an integrated electrical biosensor that can be used in couple with an electrochemical assay system. The integrated electrical biosensor may be substituted instead of the electrochemical assay system electrodes. The electrochemical assay system may be a cyclic voltammetric system or a potentiostat system.

In some implementations, the integrated electrical biosensor may include a working electrode, a counter electrode and a reference electrode designed and fabricated on a single chip, consistent with one or more aspects of the present disclosure. The working electrode, the counter electrode and the reference electrode may include arrays of SiNWs that are grown on a silicon chip. The working electrode may be the array of SiNWs electrodes that may be used to attaching cancer cells as described hereinabove in step 302.

It should be understood that the alteration of cancer cell's ionic state, induced by treating the cancer cells with an anticancer drug, can be considered as a criterion to investigate and monitoring the effect of an anticancer drug on cancer cells or in other word, the cancer cells resistance against anticancer drugs as used herein in the present disclosure. As the result, the anticancer drug treatment would change the anodic/cathodic response peaks by releasing cytochrome C in cytoplasm. Reduction of cytochrome C would change the ionic state of the cells attached to the SiNWs electrodes of the biosensor described in the present disclosure. So, the changed electrochemical response of the SiNWs after treating the cells by an anticancer drug could be translated in a well demanded electrochemical approach.

Figure 4:
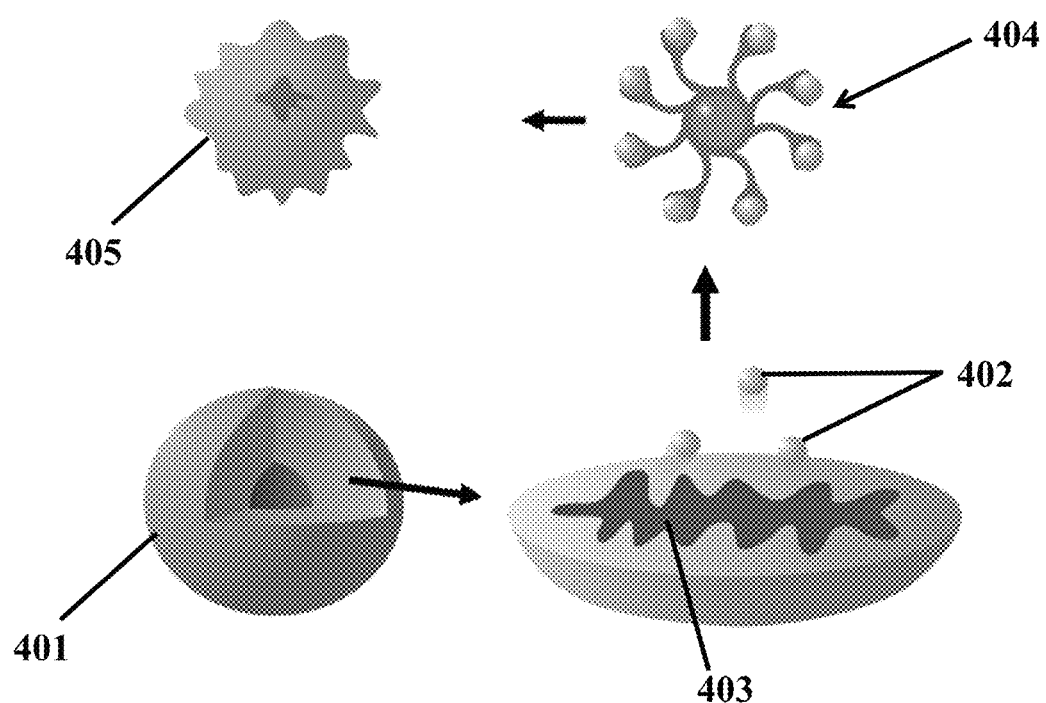
FIG. 4 illustrates an example schematic of the electrochemical affecting of an exemplary anticancer drug on an example cancer cell, consistent with one or more exemplary embodiments of the present disclosure.

FIG. 4 shows a schematic of the electrochemical effect of an example anticancer drug on an example cancer cell, representing the accumulation of cytochrome C from the mitochondria to the cytoplasm resulted in perturbation of the cancer cell's ionic or electrochemical state, consistent with one or more exemplary embodiments of the present disclosure. As shown in this figure, an exemplar MCF-7 cancer cell 401 might be treated by an exemplar MBZ anticancer drug. As a result, the cytochrome C 402 (as an active ionic agent (oxidative)) may be released from the mitochondria 403 and accumulated into the cytoplasm region (such as configuration 404 shown in FIG. 4) that would change the ionic state of cytoplasm and subsequently the ionic equilibrium between cell's inner and outer parts resulted in perturbation of the cell's ionic or electrochemical state. After about 12 hours from this accumulation, activation of caspase-9 and caspase-8 and cleavage of the caspase substrate poly(ADP-ribose) polymerase and procaspase-3 may be detectable. Ultimately, a cell death 405 may be occurred after a time interval of drug treatment. Accordingly, the difference between the first and the second electrochemical (anodic/catholic) responses of the cells attached to the SiNWs before and after the drug treatment may be used to monitor and investigate the anticancer drugs effect on the cancer cells as described in the present disclosure.

EXAMPLES

Example 1: Fabricating a SiNW-Based Biosensor

In this example, a silicon wafer substrate may be cleaned through a standard RCA #1 method (using a $NH_4OH:H_2O_2:H_2O$ solution with a volume ratio of about 1:1:5). The surface of the wafer may be then passivated by a thin layer (having a thickness of about 300 nm) of $SiO_2$ grown by wet oxidation furnace. A gold catalyst layer with a thickness of about 5 nm may be deposited on the $SiO_2$ layer using a sputtering system at a pressure of about 20 m Torr. The Au-covered wafer may be located in a low pressure chemical vapor deposition (LPCVD) system with a quartz tube chamber and the gold may be patterned by architecture of the integrated work, counter and reference electrodes. During a graining process, a thermal annealing at 450-550° C. for 30 min at the presence of argon (Ar) may be carried out which results in the catalyst graining and formation of gold nano-sized islands. The radius of the work electrode (WE) may be about 35 μm. Afterwards, during a growth step, a mixture of high purity silane ($SiH_4$) as Si source and Ar as carrier and dilution gases may be introduced to the chamber. Silicon crystalline nanostructures may be formed on top of the catalyst islands in the patterned regions followed by breaking of the silane to Si and Si—H free radicals.

Figure 5A:
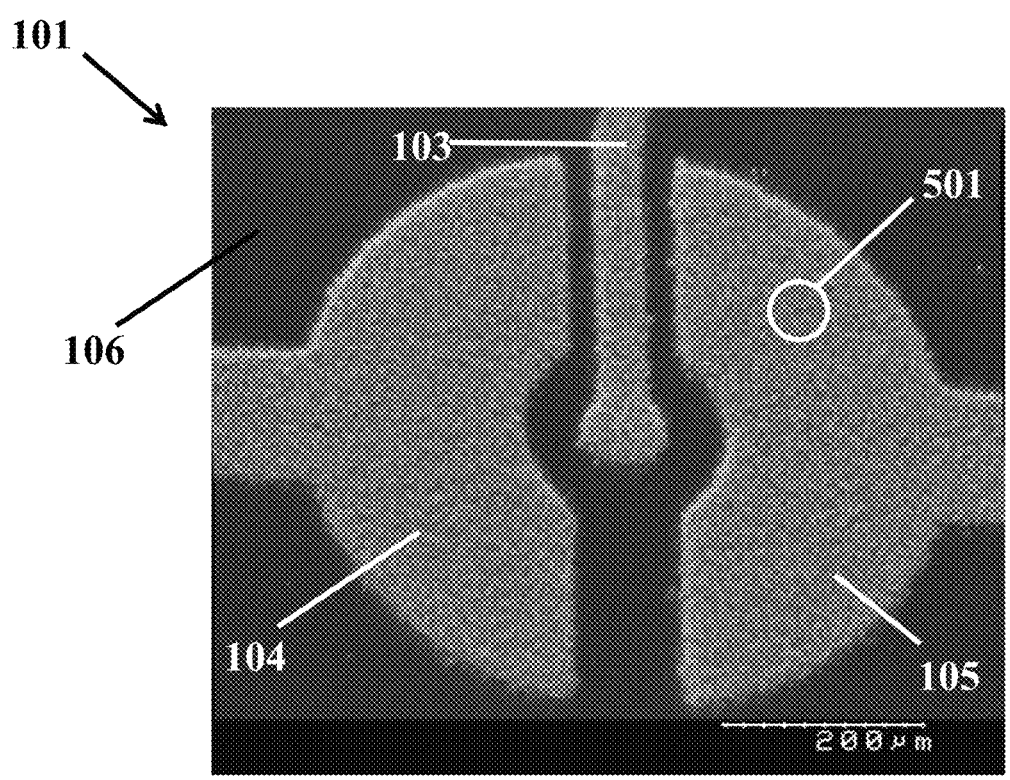
FIG. 5A illustrates a field emission scanning electron microscope (FESEM) micrograph of an example of an integrated SiNW-based sensor including the work, counter and reference electrodes, consistent with one or more exemplary embodiments of the present disclosure.

FIG. 5A shows a field emission scanning electron microscope (FESEM) micrograph of an example of an integrated SiNW-based sensor 101 designed and fabricated in the present exemplary embodiment that may include a work electrode 103, a counter electrode 104 and a reference electrode 105 that may be three arrays of SiNWs grown on a silicon chip 106, in accordance with FIG. 1 described hereinabove. It can be observed from FIG. 5A that SiNWs are present only in the patterned regions associated with the three biosensor electrodes and also have a uniform distribution.

Figure 5B:
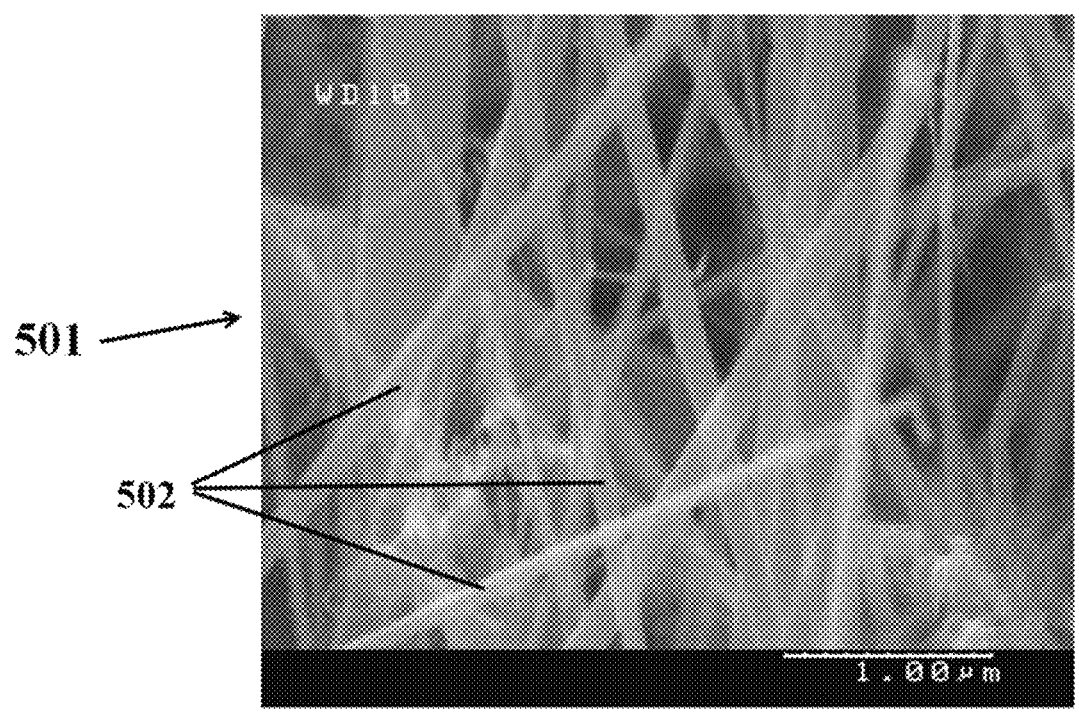
FIG. 5B illustrates a field emission scanning electron microscope (FESEM) micrograph of an example of magnified grown SiNWs of an integrated SiNW-based sensor, consistent with one or more exemplary embodiments of the present disclosure.

FIG. 5B shows a field emission scanning electron microscope (FESEM) micrograph of an example magnified section 501 in FIG. 5A, which may be placed within the grown SiNWs arrays (herein within the reference electrode 105). An array of SiNWs 502 can be observed in this figure including a plurality of silicon nanowires with a width of less than about 80 nm. The morphology and configuration of the SiNWs 502 may form a nest-like porous nanostructure with non-preferential orientations with respect to surface of the substrate (FIG. 5B). Such morphology would provide unique electrochemical characteristics due to their high surface area and excellent ability of their boundaries in sensing any electrochemically produced charges through the crystally connected net of wires.

Figure 5C:
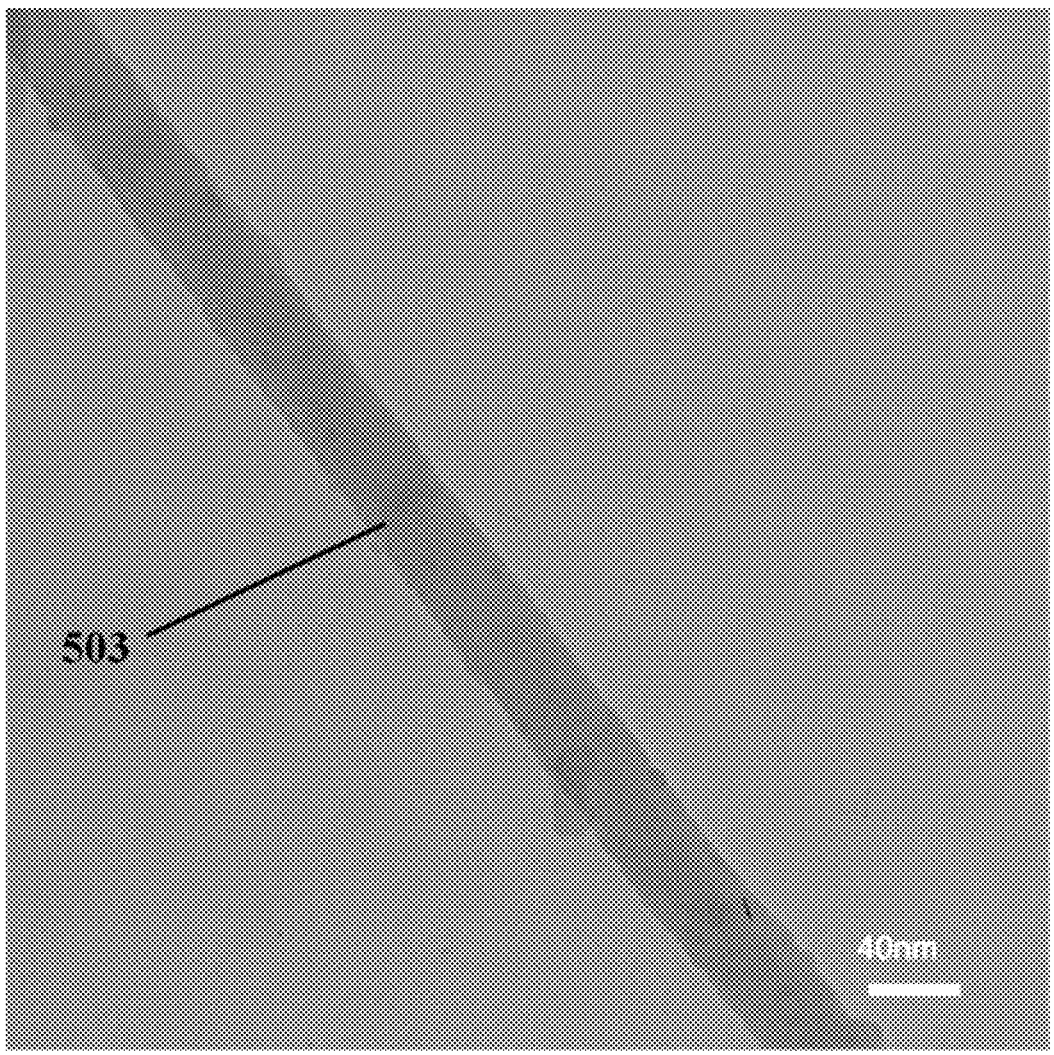
FIG. 5C illustrates a transmission electron microscope (TEM) image of an example of a single silicone nanowire (SiNW) among an array of SiNWs grown on the patterned regions of the catalyst layer, consistent with one or more exemplary embodiments of the present disclosure.

Also, a transmission electron microscope (TEM) image of an example of a single silicone nanowire (SiNW) 503 among the array 502 is shown in FIG. 5C which has a width of about 40 nm.

Figure 5D:
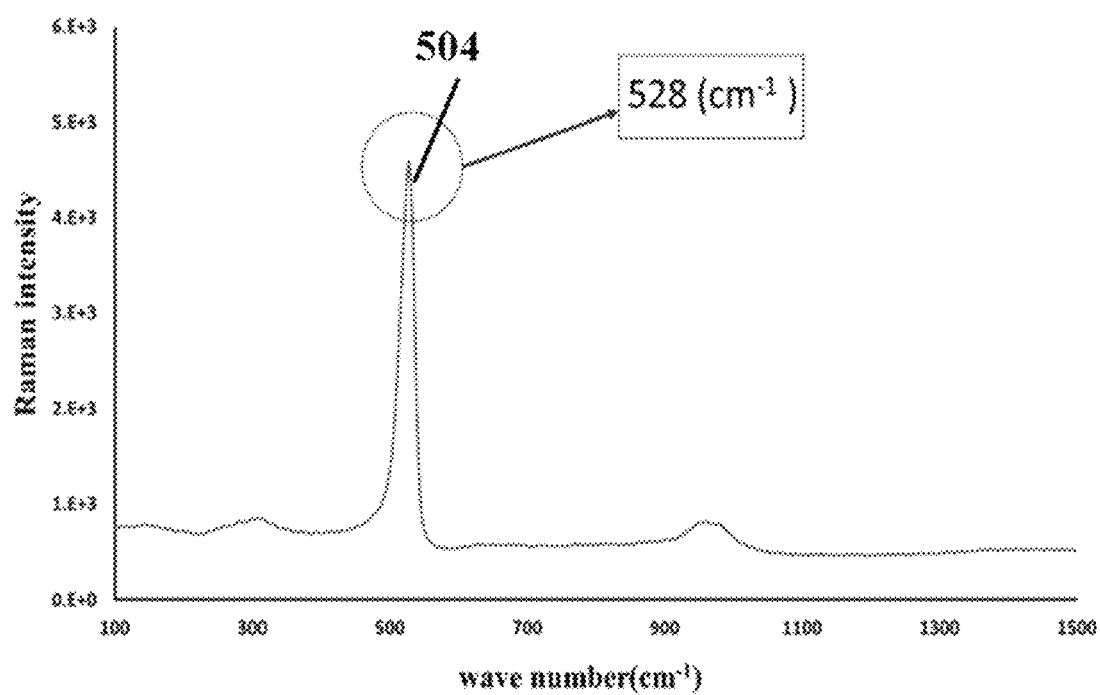
FIG. 5D illustrates a Raman spectroscopy curve of an example of the grown SiNWs, consistent with one or more exemplary embodiments of the present disclosure.

To corroborate the crystalline state of SiNWs which directly affects the SiNWs charge transfer properties, a Raman spectroscopy may be carried out which is shown in FIG. 5D. Observation of a peak 504 of Si at 528 cm$^{-1}$ indicates the crystalline nature of the grown nanowires.

Example 2: Characterization of SiNWs-Based Biosensor

In this example, the SiNW electrodes of an exemplary SiNW-based biosensor of the present disclosure may be analyzed by a cyclic voltammetry (CV) and/or a DPV assay using Ferricyanide as the reference ionic solution and substituting the exemplary biosensor fabricated in connection with Example 1 hereinabove in replace of the electrodes of a cyclic voltammetry system and/or a potentiostat system. Accordingly, the electrodes may be analyzed at a scan rate of about 100 mV/s using a 0.01 M of Ferricyanide ([Fe(CN)$_6$]$^{3-/4-}$) as reference and standard redox probe.

For CV characterization, three-electrode electrochemical cyclic voltammetry may be performed using the electrochemical workstation. Instead of the system electrodes, the SiNW-based biosensor including integrated SiNW electrodes may be used that is designed and fabricated pursuant to the teachings of the present disclosure. CV assay may be performed between the integrated SiNW covered working electrode 103 and counter electrode 104, with an on chip reference electrode 105 (represented in FIGS. 1 and 5A). The reference electrode may be initially calibrated by an Ag/AgCl reference electrode in a solution of about 1 mM ferrocene carboxylic acid with about 1 mM potassium chloride. CV studies may be performed using DC voltage and applying no AC frequency. For CV data recording, measurements may be carried out at about −0.8 V to 0.8 V at a scan rate of about 100 mv/s.

For DPV measurement, a derivative of linear sweep voltammetry, with a series of regular voltage pulses superimposed on the potential linear sweep. The current may be sampled twice, just before the pulse application and again, late in the pulse lifetime. The current may be measured immediately before each potential change, then the current difference may be plotted as a function of potential. By sampling the current just before the potential was changed, the effect of the charging current may be decreased.

Figure 6A:
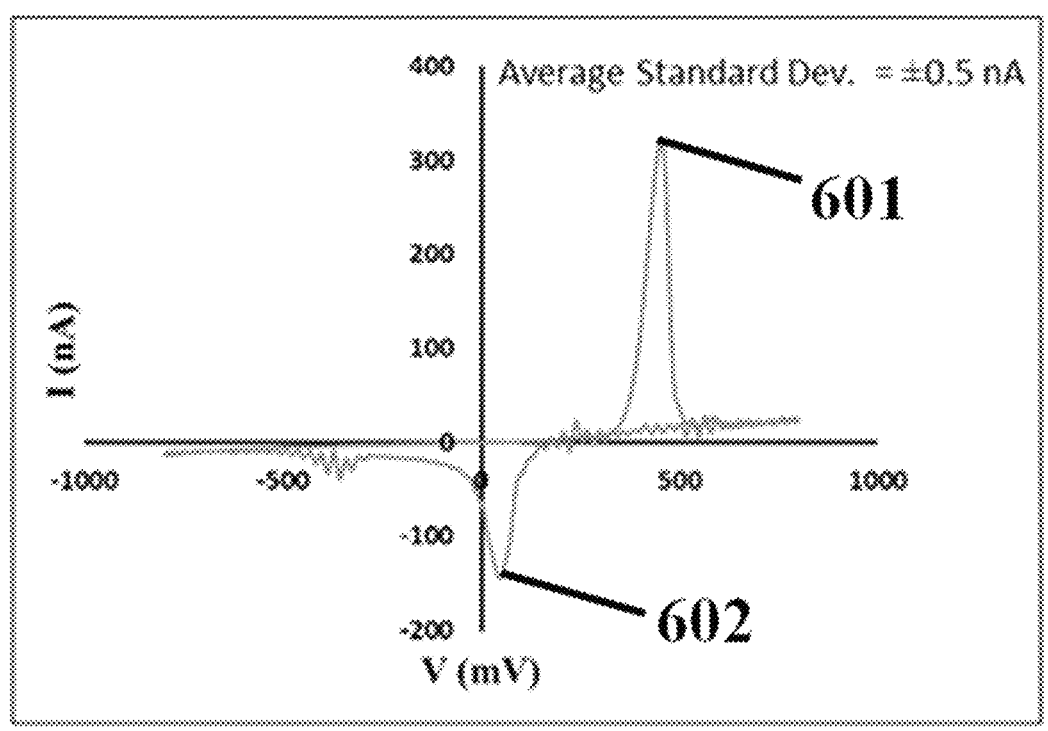
FIG. 6A illustrates a cyclic voltammetry (CV) curve of a Ferricyanide solution measured by an exemplary SiNW-based biosensor used in conjunction with a cyclic voltammetric system, consistent with one or more exemplary embodiments of the present disclosure.

FIG. 6A shows the obtained CV curve for an exemplary fabricated SiNW-based biosensor. The presence of both an anodic current peak 601 (located at 450 mV) and a cathodic current peak 602 (located at 75 mV) of SiNWs electrodes demonstrates the well electrochemical behavior of SiNWs with the great charge transfer mobility of nanowires.

Figure 6B:
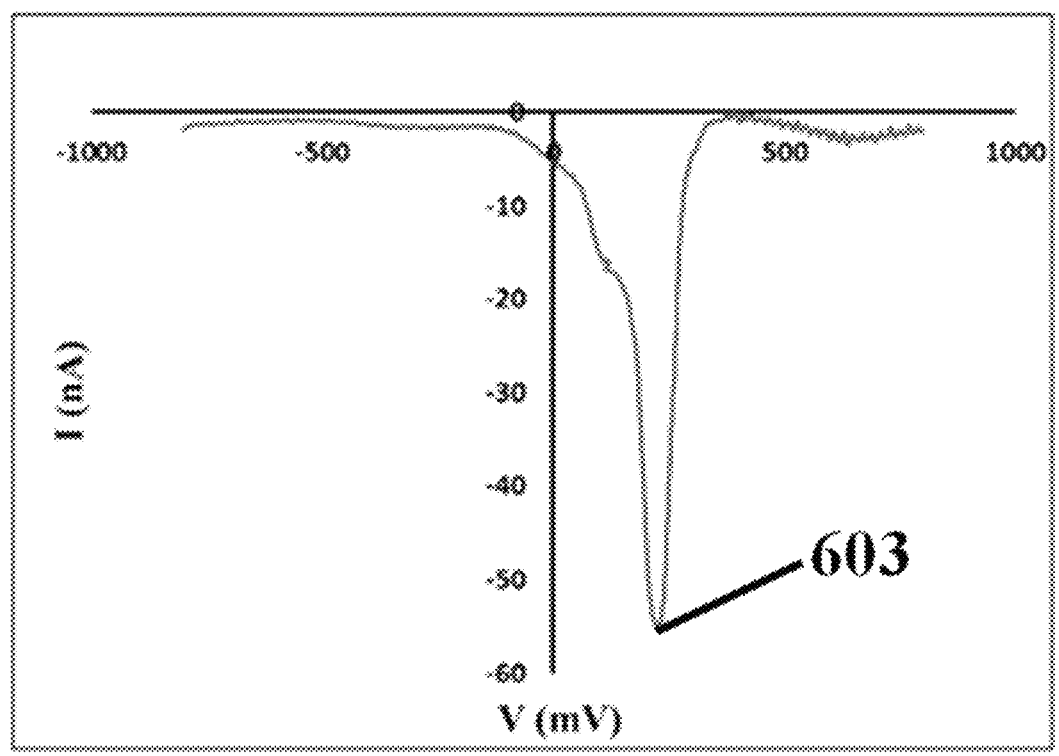
FIG. 6B illustrates a differential pulse voltammetry (DPV) curve of a Ferricyanide solution measured by an exemplary SiNW-based biosensor used in conjunction with a potentiostat system, consistent with one or more exemplary embodiments of the present disclosure.

In addition, FIG. 6B shows an example of the obtained DPV curve for an exemplary fabricated SiNW-based biosensor, wherein the SiNW electrodes are covered with [Fe(CN)$_6$]$^{3-/4-}$. Referring to this figure, the DPV response of the [Fe(CN)$_6$]$^{3-/4-}$ covered SiNW electrodes exhibits a peak current 603 of about −58 nA representing a well electrochemical behavior of SiNWs.

Example 3: Response of the SiNW-Based Sensor to the Presence of Cancer Cells

In this example, to evaluate an exemplary fabricated biosensor of the present disclosure in a cell sensing approach, the CV and DPV responses of the corresponding electrochemical systems may be experimented. The CV and DPV responses may be analyzed for three comparable situations. Initially, in the presence of cells media solution as the crucial ionic environment, then, after attachment of the cells onto the surface of SiNW work electrode and finally, after detachment the cells from the SiNWs by use of a trypsin solution.

During all experiments of the present disclosure, cells should be maintained and incubated in cells media to being alive. The RPMI1640 ionic solution (containing 10% FBS) is a cell culture media that may be used throughout all investigations. So, the electrochemical response of the media should be considered in all of experiments.

Figure 6C:
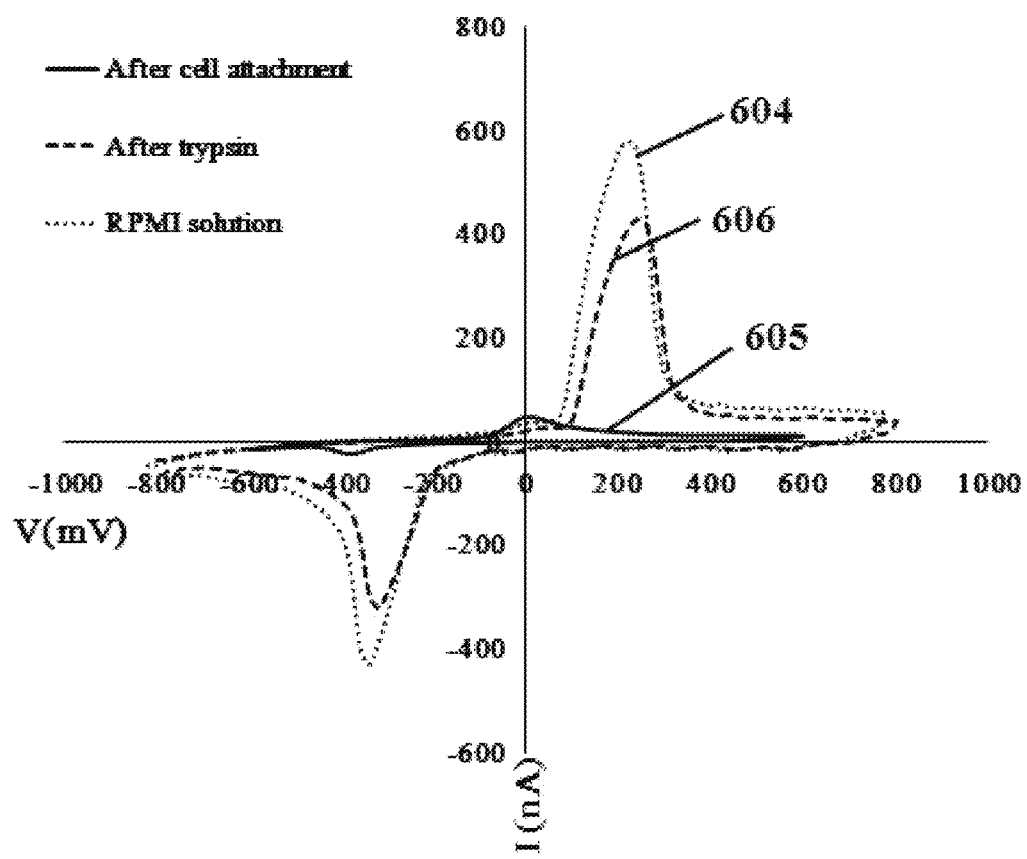
FIG. 6C illustrates cyclic voltammetry (CV) curves of an exemplary SiNW-based biosensor before and after attachment of MCF-7 cells as well as after their detachment from the surface by trypsin, consistent with one or more exemplary embodiments of the present disclosure.

FIG. 6C shows an anodic response of the RPMI detected by SiNW electrodes of an exemplary biosensor designed and fabricated pursuant to the teachings of the present disclosure, that is located at 200 mV (curve 604). High porosity/surface area of SiNWs electrodes can help to increasing the detection resolution of any ionic transfer happened in the sensing media. After attachment of Michigan Cancer Foundation-7 (herein after "MCF-7") cells—that may be used in the present study—on the surface of SiNWs, both anodic and cathodic peaks of the CV response were decreased (curve 605). It would strongly correlate with passivation of the electrodes by the attached cells as dielectric layers. Subsequently, curve 606 presents that the anodic and cathodic spikes may be again observed in the CV response of cells detached SiNWs using a trypsinization process.

Figure 6D:
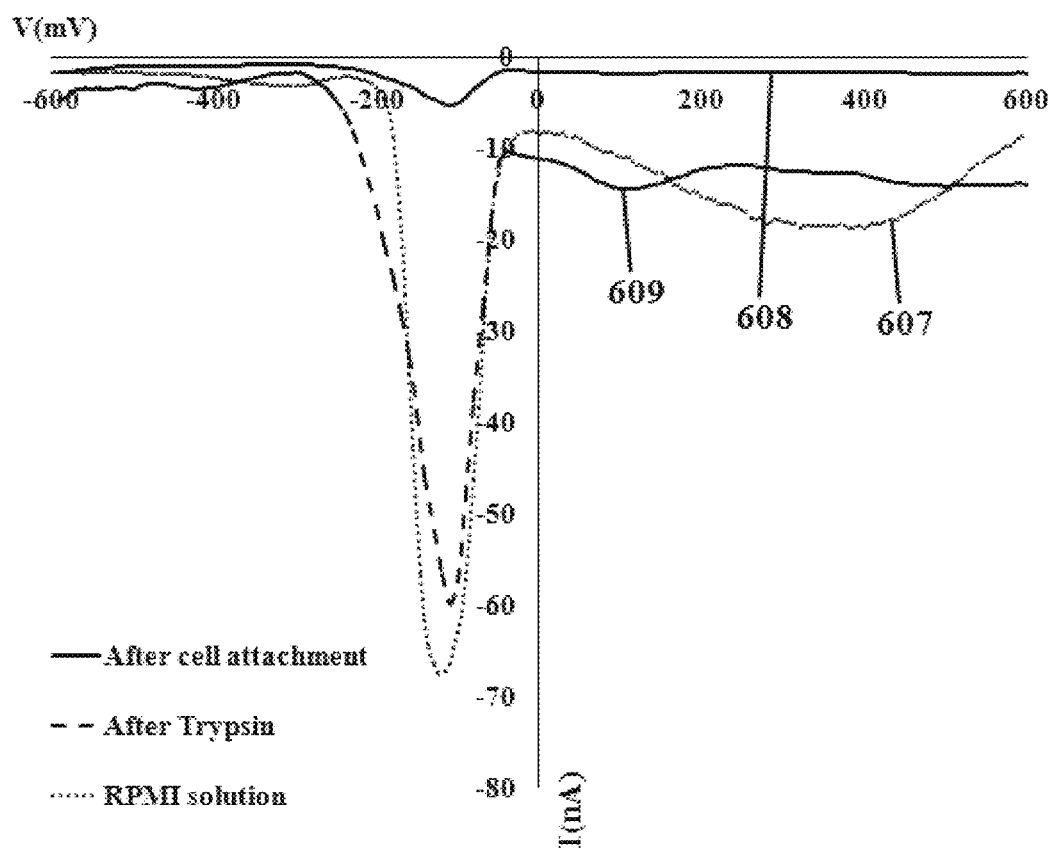
FIG. 6D illustrates differential pulse voltammetry (DPV) curves of an exemplary SiNW-based biosensor before and after attachment of MCF-7 cells as well as after their detachment from the surface by trypsin, consistent with one or more exemplary embodiments of the present disclosure.

FIG. 6D shows DPV profiles of the SiNWs electrodes of an exemplary prepared biosensor pursuant to the teachings of the present disclosure. The intensity of electrochemical DPV peak of RPMI sensed by SiNWs represents a value of about −70 nA (curve 607). The DPV profile of the SiNWs electrodes after attachment of the MCF-7 cells covering all of the effective surface of the work electrode is shown by curve 608. By comparing this voltammogram (curve 608) with DPV spectra of RPMI solution (curve 607), it is observable that the absolute DPV peak current in SiNWs has been reduced about 14 times after attachment of the cells (from about −70 nA to about −5 nA). This would be a well indication on the high interactive surface of SiNWs. The Presence of the cells on the surface of SiNWs suppressed the current flow from WE to CE and degraded the DPV spikes. When detection is not mass transport constrained, only modest enhancement is expected at the lowest concentrations. Finally, the measurements were repeated after detachment of the cells from the surface of SiNW electrodes by trypsinization. It can be seen from curve 609 that the absolute DPV peak current was increased (in negative regime) after detachment of the cells from about 5 nA to about 60 nA. Such increment would be certainly the result of removing the cells as the main agent of suppression in ionic transport between WEs and CEs. We can reveal that the remained adhesive proteins and some residues of the cells after trypsinization from the nanowires might inhibit from the precise adjustment of the peak current in its previous location (curve 609) after detachment of the cells.

Example 4: Shape and Geometry of Cancer Cells Attached on SiNW-Based Biosensor

Figure 7A:
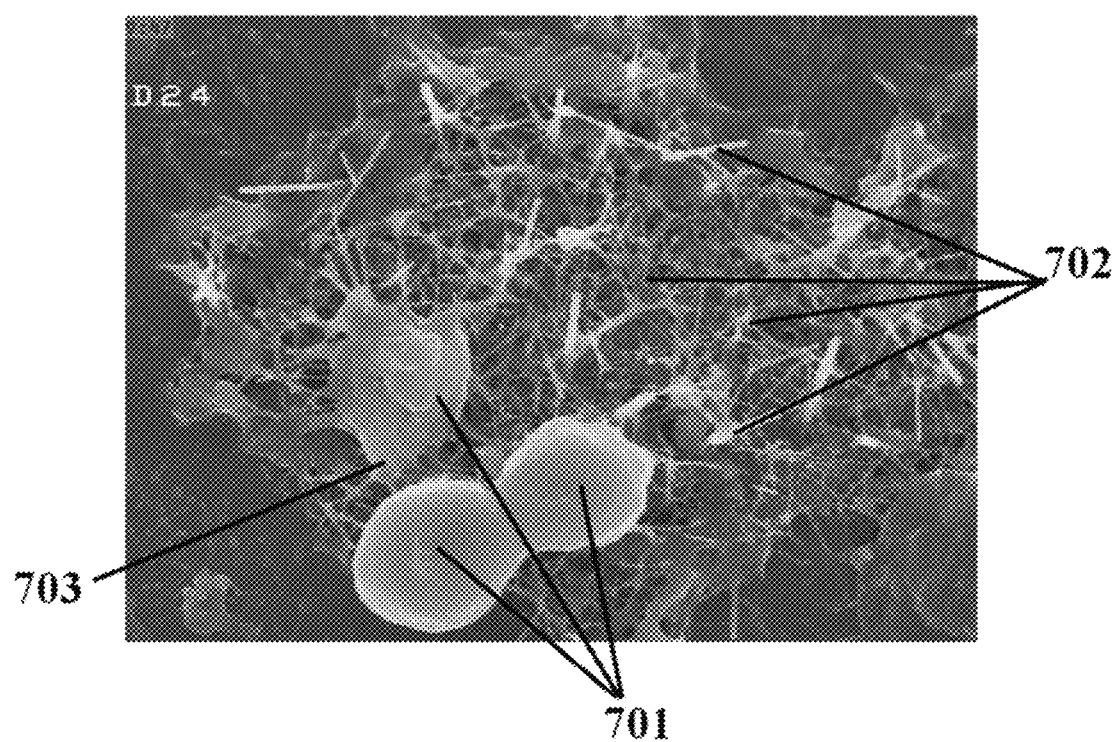
FIG. 7A illustrates a field emission scanning electron microscope (FESEM) micrograph of MCF-7 cells attached on the surface of an example of SiNWs array electrode, consistent with one or more exemplary embodiments of the present disclosure.
Figure 7B:
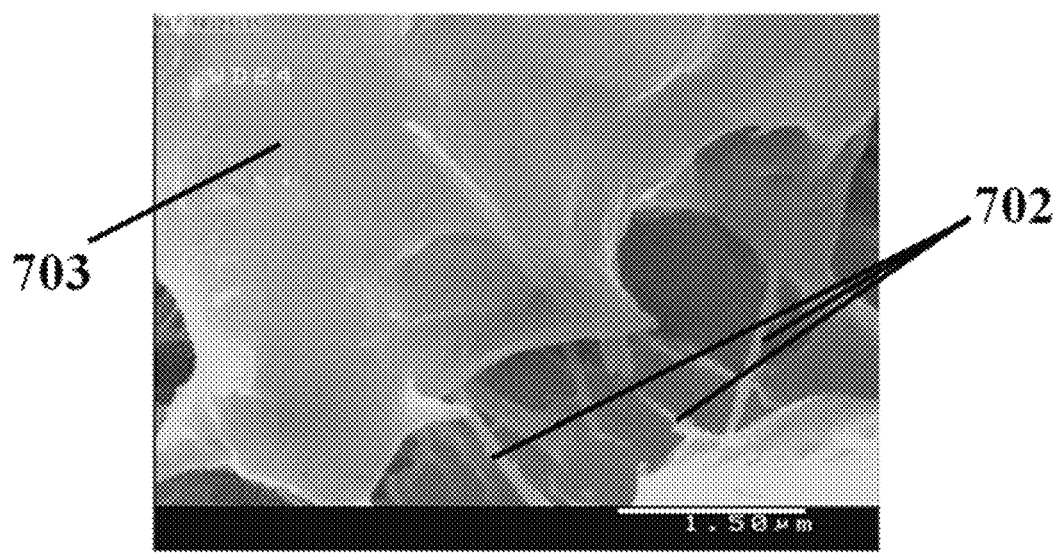
FIG. 7B illustrates a more magnified field emission scanning electron microscope (FESEM) micrograph for an exemplary single MCF-7 cell attached on the surface of SiNWs array of an example of a SiNW-based biosensor, consistent with one or more exemplary embodiments of the present disclosure.
Figure 7C:
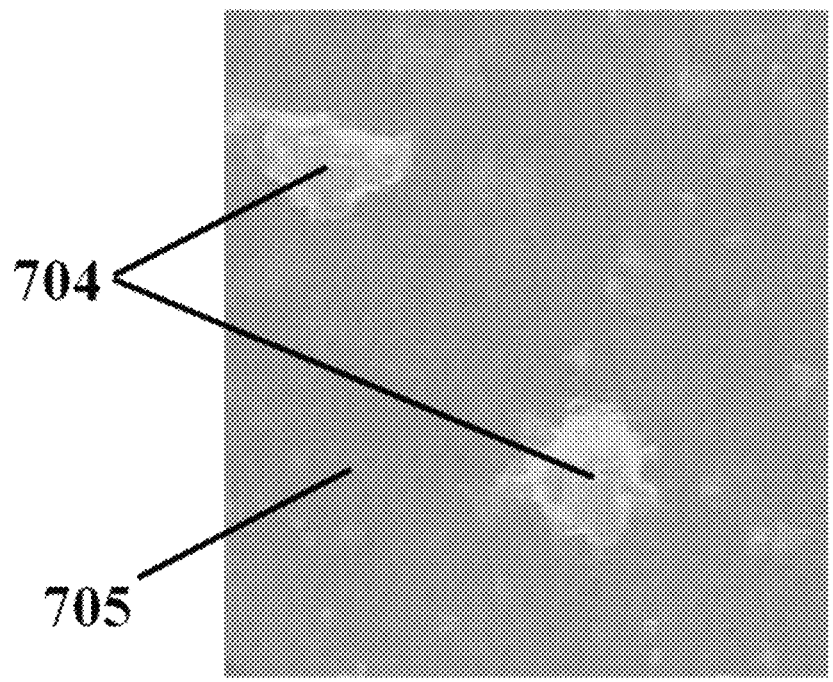
FIG. 7C illustrates a field emission scanning electron microscope (FESEM) micrograph for an exemplary single Michigan Cancer Foundation-7 (MCF-7) cell attached on the surface an exemplary bare Si electrode, consistent with one or more exemplary embodiments of the present disclosure.

FIG. 7A shows a field emission scanning electron microscope (FESEM) micrograph of exemplary MCF-7 cells 701 attached on the surface of an example of SiNWs arrays 702 of an exemplary SiNW-based biosensor of the present disclosure and in connection with the above examples. The width distribution of skein structure of SiNWs ranged from about 45 to about 110 nm induced large efficient interactive surface between a cell and nanowires, that is observable in a more focused FESEM image for an exemplary single cell 703 in FIG. 7B. The efficient interactive surface of SiNWs in the region of single cell is about 22700 $\mu m^2$ as can be measured from FESEM image of FIG. 7B, meanwhile such surface may be about 127 $\mu m^2$ for an exemplary cell 704 attached onto an exemplary bare Si electrode 705 that is shown in FIG. 7C. The SiNWs can apply direct interaction with cells because of their attachment into outer membrane all of which considerably enhance the quality of the responses.

Example 5: Anticancer Drug Resistance Assay of MCF-7 Cells Using SiNW-Based Biosensor In this example, the effect of Mebendazole (MBZ), which is an antitubulin drug that induces tubulin depolymerization in cancer cells, may be investigated via an exemplary electrochemical method of the present disclosure. The MCF-7 cells attached on SiNWs of an exemplary biosensor of the present disclosure may be treated with different doses of MBZ and the electrochemical response of an individual non-treated (hereinafter "CTRL") cell and treated cells may be monitored.

Accordingly, exemplary MCF-7 cell lines isolated from grade I human breast tumors may be used as cancer cells. The MCF-7 cells may be maintained in a $CO_2$ incubator containing about 5% $CO_2$ and at a temperature of about 37° C. in a RPMI-1640 medium supplemented with a 5% fetal bovine serum, and 1% penicillin/streptomycin. The fresh medium may be replaced every other day. Prior to each experiment, cells may be trypsinized to be detached from the substrate and re-suspended on the SiNW electrodes of an exemplary biosensor of the present disclosure. To minimize the effect of trypsinization, the procedure may be done in less than about 4 minutes at a room temperature of about 20° C. to about 22° C. The biosensor including the attached cells may be held in an incubator for about 4 hours to achieve cells attachment on the SiNWs. Then the MBZ drug with a low concentration (about 2 nano-mole per liter) and with a high concentration (about 10.5 nano-mole per liter) may be added to the cells. The signal recording and biological assays may be investigated at about 2, 6 and 10 hours after addition of the drug.

Figure 8A:
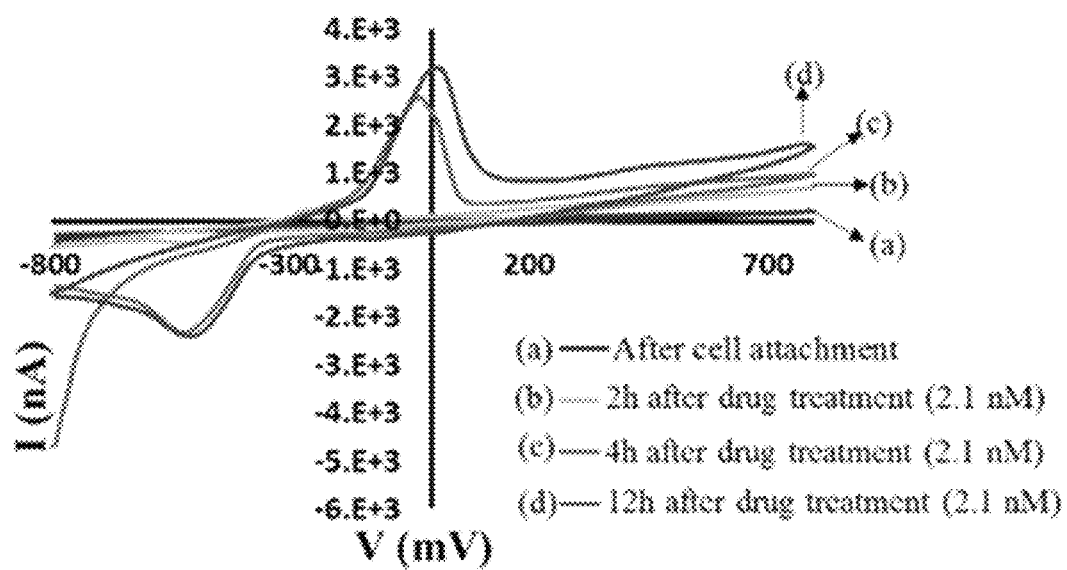
FIG. 8A illustrates cyclic voltammetry (CV) spectra of MCF-7 cells attached on an exemplary SiNW-based biosensor in various time lapses after interaction with 2 nano-mole per liter of MBZ, consistent with one or more exemplary embodiments of the present disclosure.
Figure 8B:
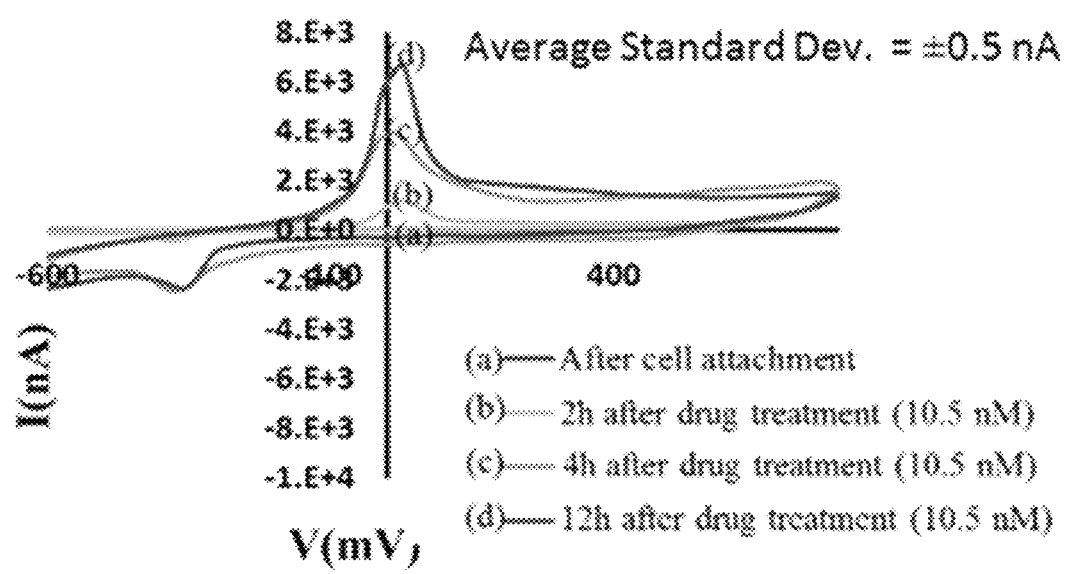
FIG. 8B illustrates cyclic voltammetry (CV) spectra of MCF-7 cells attached on an exemplary SiNW-based biosensor in various time lapses after interaction with 10.5 nano-mole per liter of MBZ, consistent with one or more exemplary embodiments of the present disclosure.

FIGS. 8A and 8B represent the CV diagrams of CTRL and MBZ treated samples with individual MBZ concentrations of about 2 nano-mole per liter (FIG. 8A) and about 10.5 nano-mole per liter (FIG. 8B). Both anodic and cathodic spikes may be observed in CV diagrams just 2 hours after drug incubation with the cells. By increasing the dose of MBZ to about 10.5 nano-mole per liter, the height of the CV spikes increased by nearly three orders (FIG. 8B).

Figure 8C:
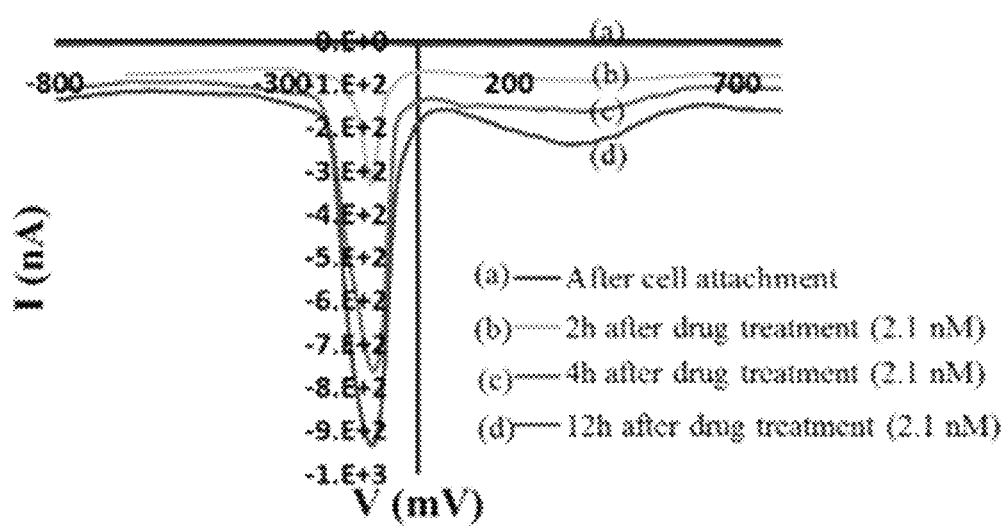
FIG. 8C illustrates differential pulse voltammetry (DPV) spectra of MCF-7 cells attached on an exemplary SiNW-based biosensor in various time lapses after interaction with 2 nano-mole per liter of MBZ, consistent with one or more exemplary embodiments of the present disclosure.
Figure 8D:
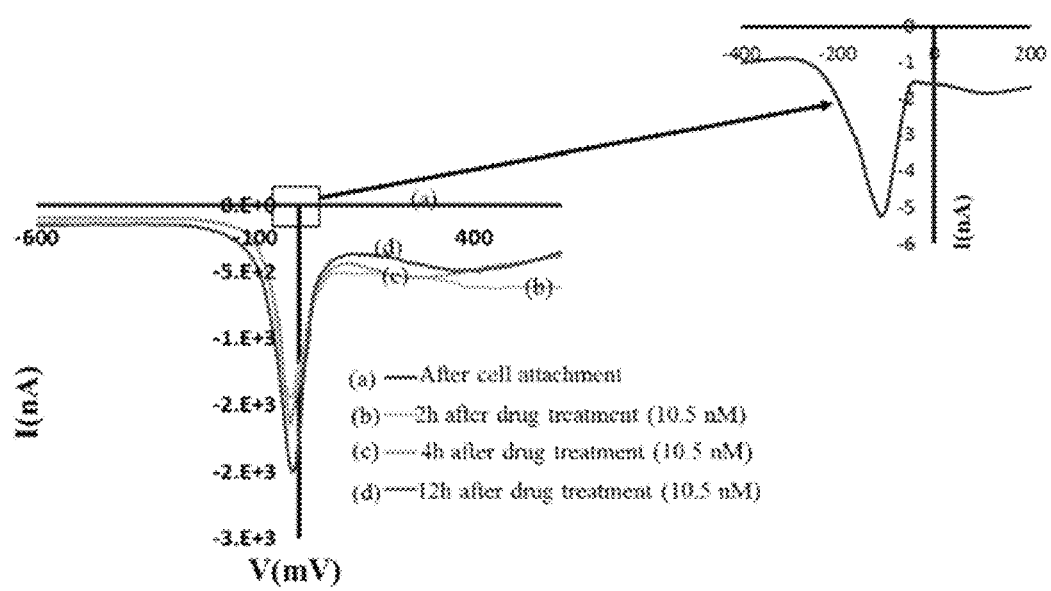
FIG. 8D illustrates differential pulse voltammetry (DPV) spectra of MCF-7 cells attached on an exemplary SiNW-based biosensor in various time lapses after interaction with 10.5 nano-mole per liter of MBZ, consistent with one or more exemplary embodiments of the present disclosure.

Correspondingly, FIGS. 8C and 8D represent the DPV diagrams of CTRL and MBZ treated samples with individual MBZ concentrations of about 2 nano-mole per liter (FIG. 8C) and about 10.5 nano-mole per liter (FIG. 8D). FIG. 8C indicated that just about 2 nano-mole per liter of MBZ may seriously affect the electrochemical response of cancer cells in about 2 hours. Absolute DPV current peaks of the SiNW-based biosensor just 2 hours after cells treatment by about 2 nano-mole per liter of MBZ increased from about 5 nA to about 300 nA. About 12 hours after the treatment, the intensities of the absolute DPV peaks reached to about 900 nA. Absolute DPV of higher dose MBZ (about 10.5 nano-mole per liter) treated cells increased to about 1400 after 2 hours and to about 2000 nA and 12 hours (FIG. 8D).

The Sharp electrochemical response of the MBZ treated MCF-7 cells might be assigned to cells functional perturbations caused by drug induced Microtubule depolymerization. The great charge mobility among the net of silicon nanowires, the excellent capability for exchange of electrons at the nanowalls, the ballistic mobility of electrons in silicon nanocrystalline structure and/or direct attachment of thin rounded nanowalls into the cells might all be effective in the well response of SiNWs electrodes to electrochemical variations in drug-treated cancer cells.

Figure 9A:
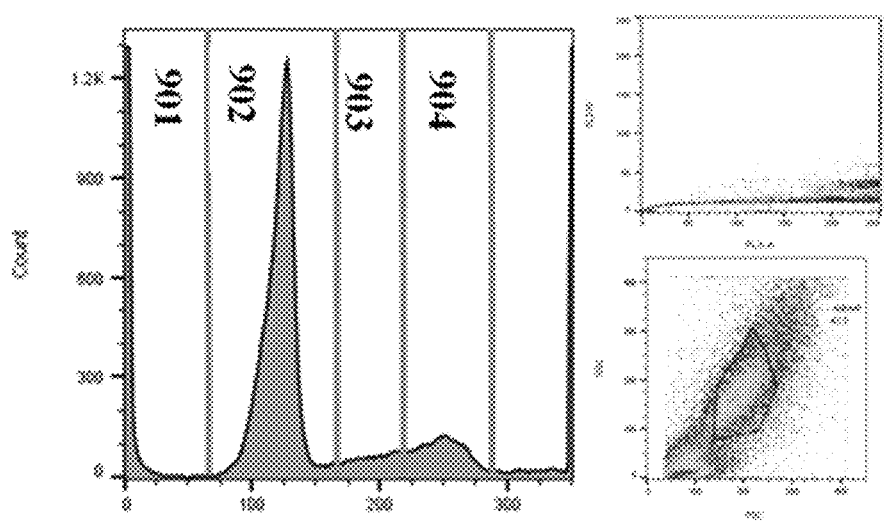
FIG. 9A illustrates flowcytometry analysis curve (Left side) and the state of counted cells (Right side) of MCF-7 cells in the absence of an anticancer drug.
Figure 9B:
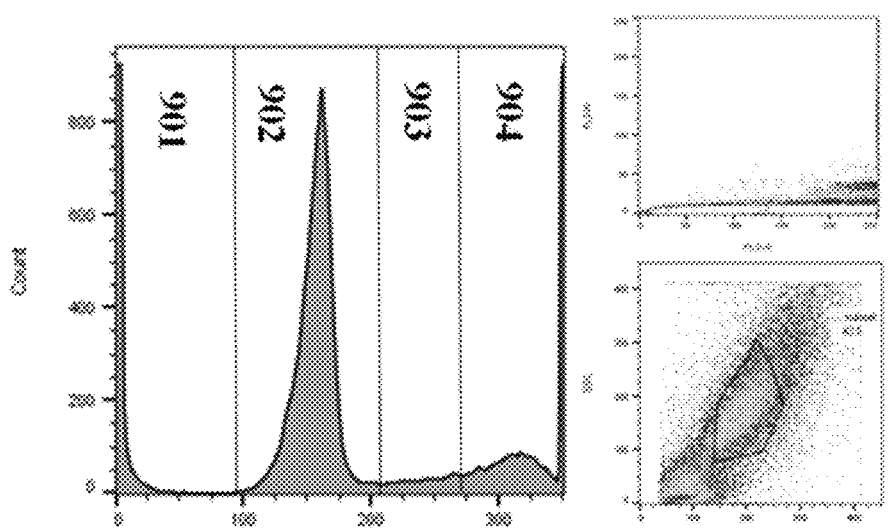
FIG. 9B illustrates flowcytometry analysis curve (Left side) and the state of counted cells (Right side) of MCF-7 cells treated with MBZ with a concentration of about 2 nano-mole per liter.
Figure 9C:
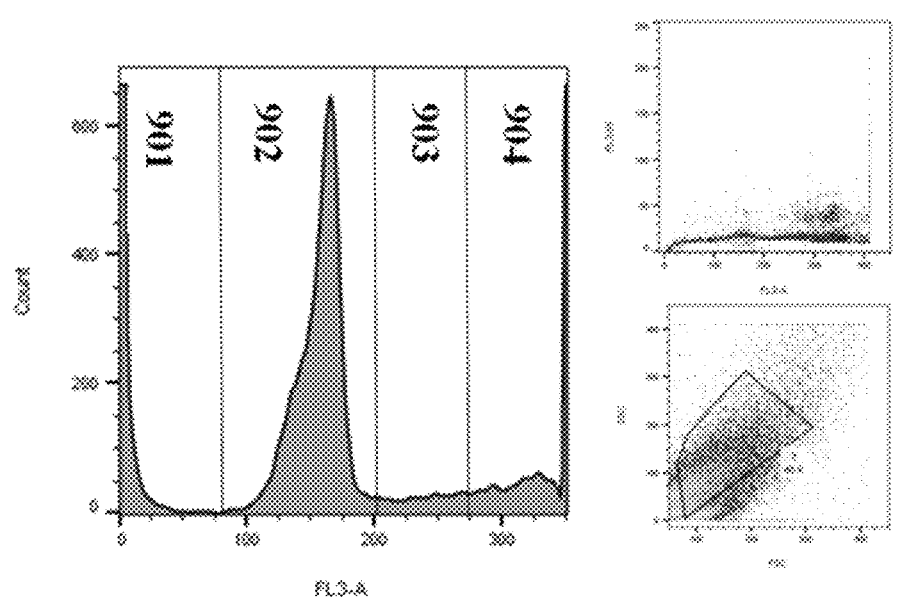
FIG. 9C illustrates flowcytometry analysis curve (Left side) and the state of counted cells (Right side) of MCF-7 cells treated with MBZ with a concentration of about 10.5 nano-mole per liter.

In addition, cell cycle progression for CTRL and drug treated MCF-7 cells may be determined by flowcytometry analysis that are shown in FIG. 9A (for CTRL cells), FIG. 9B (for treated cells with about 2 nano-mole per liter of MBZ) and FIG. 9C (for treated cells with about 10.5 nano-mole per liter of MBZ). The cell's fractions in apoptotic (part 901), G0/G1 (part 902), S (part 903) and G2/M (part 904) cycles are observable in all of panels. Also, the state of counted cells for each of these three situations is represented at the Right side of the figures. These figures show that various concentrations of MBZ induced non similar effects on the cycles and states of the cells. The part 901 representing apoptotic cells with hypodiploid DNA (subG1 fraction) has been slightly increased in low concentration drug treated sample (FIG. 9B) comparing with CTRL sample (FIG. 9A). This reveal that MBZ (about 2 nano-mole per liter) did not induce the apoptotic behavior of MCF-7 cells. But, proportion of G0/G1 fraction (part 902) was changed in MBZ incubated samples. The peak of G0/G1 was about 1300 in CTRL sample (FIG. 9A) meanwhile it was reduced to about 800 in MBZ (about 2 nano-mole per liter) treated cells (FIG. 9B). The result can be confirmed by side scatter versus forward scatter (SSC-FSC) diagram as a strong sign of cells granularity (represented at Right side of FIGS. 9A, 9B and 9C). In addition, the G2/M fraction (part 904) in MBZ (about 2 nano-mole per liter) treated sample shown in FIG. 9B is less than half of measured for CTRL (FIG. 9A). By increasing the dose of MBZ to about 10.5 nM (FIG. 9C), apoptotic behavior (part 901) of the cells was affected. Also, sharper reduction in the amount of the cells in G0/G1 phase (part 902) was observed in similar time. Such disorders in the cycle of the cells after MBZ treatment would be well demanded by affected anodic/cathodic response of the cells measured by SiNWs electrodes.

What is claimed is:
1. An electrochemical method for detecting effect of an anticancer drug on cancer cells, comprising:
   culturing a plurality of cancer cells onto a substrate in a controlled set of conditions to form cultured cells;
   attaching the cultured cells onto an array of electrodes, the array of electrodes comprising an array of silicon nanowires (SiNWs);
   measuring a first electrochemical response of the attached cells onto the array of electrodes, comprising:
      applying a set of applied voltages between −0.8 V and 0.8 V to the array of SiNWs; and
      measuring a first set of electrical currents at the set of applied electrical voltages;
   adding an anticancer drug to the attached cells onto the array of electrodes to form drug-treated cells;
   measuring a second electrochemical response of the drug-treated cells, comprising:

applying the set of applied voltages between −0.8 V and 0.8 V to the array of SiNWs; and measuring a second set of electrical currents at the set of applied electrical voltages; and determining the effect of the anticancer drug on the cancer cells based on a comparison of the first and the second electrochemical responses, wherein:

each of the first and the second electrochemical responses comprises at least one of a cyclic voltammetry (CV) response, a differential pulse voltammetry (DPV) response, and combinations thereof, and each of the first electrochemical response and the second electrochemical response comprises a respective curve of electrical current values versus the set of applied voltages with a respective electrical current peak.

2. The method according to claim 1, wherein determining the effect of the anticancer drug on the cancer cells based on a comparison of the first and the second electrochemical responses comprises determining that the anticancer drug is effective if the second electrochemical response undergoes a change in shape and value versus the first electrochemical response and determining that the anticancer drug is not effective if the second electrochemical response does not undergo a change in shape and value versus the first electrochemical response.

3. The method according to claim 2, wherein determining the effect of the anticancer drug on the cancer cells based on the comparison of the first and the second electrochemical responses comprises:

determining that the anticancer drug is effective if the second electrochemical response undergoes an increase in electrical current value of the respective electrical current peak versus the electrical current value of the respective electrical current peak of the first electrochemical response; and determining that the anticancer drug is not effective if the second electrochemical response does not undergo a change in the electrical current value of the electrical current peak versus the electrical current value of the respective electrical current peak of the first electrochemical response.

4. The method according to claim 1, wherein adding the anticancer drug comprises:

adding a specific amount of the anticancer drug on the attached cells onto the array of electrodes; and maintaining the array of electrodes including the attached cells with the added anticancer drug at specific conditions.

5. The method according to claim 4, wherein maintaining the array of electrodes including the attached cells with the added anticancer drug at specific conditions comprises maintaining an incubator at a temperature of about 37° C. and for at least 2 hours.

6. The method according to claim 4, wherein:

the anticancer drug comprises an antitubulin drug, and the anticancer drug has a concentration in a range of 0.1 nano-mole per liter to 20 nano-mole per liter.

7. The method according to claim 1, wherein:

the cancer cells are epithelial cancer cells; and the controlled set of conditions comprises maintaining the cancer cells in a $CO_2$ incubator at a temperature of about 37° C., the $CO_2$ incubator comprises a composition of $CO_2$ and clean air.

8. The method according to claim 7, wherein the $CO_2$ has a percentage of about 5% and the clean air has a percentage of about 95%.

9. The method according to claim 1, wherein attaching the cultured cells onto an array of electrodes comprises:

detaching the cultured cells from the substrate;

dropping the detached cells on the array of electrodes; and maintaining the array of electrodes at specific conditions to achieve an attachment between the dropped cultured cells and the electrodes.

10. The method according to claim 9, wherein detaching the cultured cells from the cell culture media is carried out by a trypsinizing method for less than 4 minutes and at room temperature of 20° C.

11. The method according to claim 9, wherein maintaining the array of electrodes at specific conditions comprises maintaining the array of electrodes in an incubator for about 4 hours and at a temperature of about 37° C.

12. The method according to claim 1, wherein the measuring the first and the second electrochemical responses is done using an integrated biosensor in conjunction with an electrochemical assay system which comprises a cyclic voltammetric system or a potentiostat system.

13. The method according to claim 12, wherein the integrated biosensor comprises:

a working electrode comprising a first array of silicon nanowires (SiNWs), configured to be an attachment site for the biological cells, the first array of SiNWs comprising the array of electrodes onto which the cultured cells are attached, a counter electrode comprising a second array of SiNWs, configured to acquire the electrical response from the working electrode, a reference electrode comprising a third array of SiNWs, configured to adjust a specific voltage around the working and the counter electrodes, wherein, the working electrode, the counter electrode and the reference electrode are designed and fabricated in an integrated configuration on a chip.

14. The method according to claim 1, wherein determining the effect of the anticancer drug on the cancer cells based on a comparison of the first and the second electrochemical responses comprises comparing the respective electrical current peak of the first electrical response with the respective electrical current peak of the second electrical response.

\* \* \* \* \*